United States Patent
Lewis et al.

(10) Patent No.: US 9,321,816 B2
(45) Date of Patent: Apr. 26, 2016

(54) EXPRESSION SYSTEMS AND METHODS OF PRODUCING SPIDER SILK PROTEINS

(71) Applicants: Randolph V. Lewis, Nibley, UT (US); Charles D. Miller, North Logan, UT (US); Asif Rahman, Logan, UT (US); Cody Tramp, Logan, UT (US); Michael Hinman, Logan, UT (US)

(72) Inventors: Randolph V. Lewis, Nibley, UT (US); Charles D. Miller, North Logan, UT (US); Asif Rahman, Logan, UT (US); Cody Tramp, Logan, UT (US); Michael Hinman, Logan, UT (US)

(73) Assignee: Utah State University, North Logan, UT (US)

( * ) Notice: Subject to any disclaimer, the term of this patent is extended or adjusted under 35 U.S.C. 154(b) by 0 days.

(21) Appl. No.: 14/042,183

(22) Filed: Sep. 30, 2013

(65) Prior Publication Data
US 2014/0093965 A1    Apr. 3, 2014

Related U.S. Application Data

(60) Provisional application No. 61/707,571, filed on Sep. 28, 2012.

(51) Int. Cl.
C12N 15/70 (2006.01)
C07K 14/435 (2006.01)
C12P 21/02 (2006.01)

(52) U.S. Cl.
CPC .......... C07K 14/43518 (2013.01); C12N 15/70 (2013.01); C12P 21/02 (2013.01)

(58) Field of Classification Search
None
See application file for complete search history.

(56) References Cited

U.S. PATENT DOCUMENTS

| 5,728,810 | A | 3/1998 | Lewis et al. |
| 5,733,771 | A | 3/1998 | Lewis et al. |
| 5,756,677 | A | 5/1998 | Lewis et al. |
| 5,989,894 | A | 11/1999 | Lewis et al. |
| 5,994,099 | A | 11/1999 | Lewis et al. |
| 7,057,023 | B2 | 6/2006 | Islam et al. |
| 7,157,615 | B2 | 1/2007 | Karatzas et al. |
| 7,288,391 | B2 | 10/2007 | Roth et al. |
| 7,521,228 | B2 | 4/2009 | Lewis et al. |
| 7,723,109 | B2 | 5/2010 | Lewis |

FOREIGN PATENT DOCUMENTS

RU    2444527 C2    3/2012

OTHER PUBLICATIONS

Xia et al., PNAS, 2010, vol. 107 pp. 14059-14063.*
Hinman et al., Trends in Biotechnology, 2000, vol. 18 pp. 374-379.*
Notification of Transmittal of the International Search Report and the Written Opinion of the International Searching Authority, or the Declaration, for PCT/US2013-062722, filed Sep. 30, 2013, Mail date of Written Opinion is Dec. 19, 2013.
Xia, et al., Native-sized recombinant spider silk protein produced in metabolically engineered *Escherichia coli* results in a strong fiber, Proc. Natl. Acad. Sci, vol. 107, No. 32, pp. 14059-14063 (Aug. 10, 2010).
Brooks, et al., Properties of Synthetic Spider Silk Fibers Based on Argiope aurantia MaSp2, Biomacromolecules, vol. 9, pp. 1506-1510 (2008).
Rahman, et al., Secretion of Polyhydroxybutyrate in *Escherichia coli* Using a Synthetic Biological Engineering Approach, Journal of Biological Engineering, 7:24, (2013).
Linton, et al., Translocation of Green Fluorescent Protein by Comparative Analysis With Multiple Signal Peptides, Biotechnol. J., 6, (2011).

* cited by examiner

Primary Examiner — Michele K Joike
Assistant Examiner — Mindy G Brown

(57) ABSTRACT

An expression system, including a host cell, a synthetic spider silk polypeptide-encoding nucleotide sequence, at least one synthetic tRNA molecule-encoding nucleotide sequence or a synthetic serine hydroxymethyl transferase (SHMT)-encoding nucleotide sequence.

18 Claims, 23 Drawing Sheets

AAGCTTCATATGACCGGTGGTGCAGGTCAGGGTGGTTATGGTGGTCTG
GGTAGCCAGGGTGCCGGTCGTGGTGGACTGGGTGGTCAAGGTGCTGGT
GCAGCAGCAGCTGCCGCAGCAGCAGGCGGTGCAGGCCAAGGCGGATA
TGGCGGACTGGGTTCACAGGGTGCAGGCCGTGGCGGTTTAGGTGGTCA
AGGCGCAGGCGCTGCTGCAGCCGCAGCGGCAGCAGCTGGCCAAGGTG
GCTATGGTGGCTTAGGCTCACAGGGTGGCGGTGCTGGACAGGGTGGAT
ACGGTGGCCTTGGCAGTCAAGGTGCGGGTCGCGGTGGTTTAGGCGGTC
AGGGTGCGGGTGCGGCTGCTGCAGCTGCGGCAGCGGGTGGTGCTGGG
CAAGGCGGTTACGGTGGATTAGGTAGCCAAGGTGCAGGACGCGGAGG
TCTTGGTGGACAGGGTGCTGGCGCTGCTGCGGCAGCAGCAGCCGCTGG
GGGTGCTGGTCAAGGGGGTTATGGCGGTTTAGGATCTCAGGGTGCGGG
ACGGGGTGGTCTGGGAGGGCAAGGGGCAGGCGCAGCAGCAGCGGCAG
CTGCAGCCGGTGGTGCCGGACAAGGGGGATATGGGGGTCTTGGCTCCC
AAGGCGCTGGTCGTGGCGGTCTTGGAGGCCAAGGTGCCGGTGCCGCTG
CAGCGGCTGCTGCTGCAGCGGGTCAAGGGGGATACGGTGGTCTGGGA
TCACAAGGTGGTGGCGCAGGGCAAGGTGGGTATGGGGGTTTAGGTTC
GCAAGGTGCTGGCCGTGGGGGACTGGGAGGACAGGGTGCCGGTGCGG
CAGCCGCTGCAGCTGCTGCGGGTGGCGCTGGTCAGGGTGGCTATGGCG
GATTGGGCTCTCAAGGGGCAGGTCGGGGTGGCTTGGGAGGACAAGGT
GCGGGTGCAGCCGCTGCGGCAGCTGCCGCTGGCGGAGCAGGCCAGGG
TGGCTACGGTGGACTGGGTTCCCAAGGTGCGGGAAGAGGTGGCTTGG
GTGGCCAGGGTGCAGGGGCAGCGGCTGCAGCGGCAGCAGCCTCCGGA
GGGGATCC

AAGCTTCATATGACCGGTCCGGGTCAGCAGGGTCCGGGTGGTTATGGT
CCTGGCCAGCAGGGACCGAGCGGTCCGGGTAGTGCAGCAGCAGCTGC
AGCAGCCGCAGGCCCTGGTCAGCAAGGCCCTGGTGGATATGGACCAG
GCCAACAGGGTCCTGGCGGATACGGTCCTGGTCAACAAGGTCCGTCAG
GTCCGGGTTCAGCCGCAGCGGCTGCTGCCGCAGCAGGTCCAGGTGGCT
ACGGACCGGGTCAACAGGGACCCGGTGGGTACGGACCAGGACAGCAA
GGGCCAGGCGGTTATGGCCCTGGACAACAAGGGCCTAGTGGTCCTGGT
TCTGCAGCGGCAGCCGCTGCGGCAGCTGGTCCGGGACAGCAAGGACC
CGGTGGATACGGTCCCGGTCAGCAGGGACCTGGCGGTTACGGACCCG
GACAACAGGGTCCATCTGGTCCTGGTAGCGCAGCCGCAGCAGCAGCG
GCTGCAGGTCCAGGACAACAAGGTCCTGGTGGGTATGGTCCAGGGCA
GCAAGGTCCGAGTGGTCCAGGCTCTGCGGCAGCGGCAGCAGCAGCAG
CGGGACCTGGTCAACAGGGTCCAGGGGGATATGGCCCAGGTCAGCAA
GGACCGGGTGGCTATGGGCCAGGTCAACAAGGCCCTAGCGGTCCGGG
ATCTGCCGCAGCTGCAGCGGCAGCGGCAGGTCCTGGCGGTTATGGACC
AGGTCAGCAGGGTCCCGGTGGCTACGGTCCCGGACAACAAGGCCCAG
GGGGTTACGGACCTGGCCAGCAAGGTCCTTCTGGACCGGGAAGCGCTG
CAGCCGCAGCAGCTGCAGCCGGTCCAGGCCAGCAAGGGCCTGGGGGT
TACGGTCCGGGTCAGCAAGGCCCAGGCGGATACGGTCCAGGACAACA
GGGACCAAGTGGTCCGGGATCAGCAGCCGCTGCCGCAGCGGCAGCCG
GTCCCGGTCAACAAGGACCTGGTGGCTACGGTCCTGGGCAACAGGGTC
CTAGCGGTCCAGGGTCAGCAGCAGCAGCCGCAGCTGCAGCATCCGGA
GGGGATCC

AAGCTTCATATGACCGGTGGTGCCGGTGGTTATGGTCGTGGTGCTGGT
GCGGGTGCCGGTGCAGCAGCTGGTGCCGGTGCTGGCGCAGGCGGTTAT
GGTGGTCAGGGTGGCTACGGTGCCGGTGCCGGTGCTGGTGCCGCAGCC
GCAGCGGGTGCGGGTGCAGGCGGTGCTGGCGGTTATGGCAGAGGTGC
TGGGGCTGGTGCAGGCGCTGCAGCCGGTGCGGGTGCTGGTGCGGGTG
GATATGGTGGCCAGGGTGGTTATGGCGCTGGCGCAGGGGCAGGCGCA
GCAGCAGCAGCTGGGGCAGGCGCAGGCGGTGCCGGTGGCTATGGACG
CGGAGCCGGTGCCGGTGCAGGGGCAGCAGCGGGTGCTGGTGCCGGTG
CAGGGGGTTATGGTGGCCAAGGCGGATATGGTGCGGGTGCAGGCGCT
GGTGCAGCAGCAGCCGCTGGTGCCGGTGCCGGTGGTGCGGGTGGCTAC
GGAAGAGGTGCGGGTGCCGGTGCCGGTGCTGCAGCGGGTGCGGGTGC
GGGTGCCGGTGGTTATGGCGGTCAGGGTGGGTATGGTGCGGGTGCTGG
TGCAGGCGCAGCTGCAGCCGCTGGTGCTGGTGCAGGCGGAGCCGGTG
GATATGGCCGAGGTGCTGGCGCAGGCGCTGGCGCTGCTGCTGGTGCCG
GTGCGGGTGCTGGGGGATACGGTGGTCAAGGGGGTTATGGTGCGGGT
GCCGGTGCGGGTGCAGCCGCAGCAGCTGGTGCGGGTGCGGGTGGTGC
AGGGGGATATGGCCGTGGTGCCGGTGCTGGTGCGGGTGCTGCAGCCG
GTGCTGGGGCAGGGGCTGGCGGTTATGGGGGTCAAGGCGGTTATGGC
GCTGGTGCTGGTGCTGGGGCTGCCGCAGCAGCCGGTGCTGGTGCTGGC
GGTGCGGGTGGTTACGGTCGGGGAGCTGGCGCTGGTGCTGGCGCAGC
AGCGGGTGCCGGTGCTGGTGCCGGTGGCTACGGTGGACAAGGTGGCT
ATGGTGCCGGTGCAGGCGCAGGGGCTGCAGCCGCAGCCGGTGCCGGT
GCCGGTGGCGCTGGGGGTTATGGTCGCGGAGCGGGTGCAGGCGCAGG
CGCAGCCGCTGGCGCTGGTGCGGGTGCTGGCGGTTATGGTGGACAAGG
GGGTTATGGGGCTGGTGCTGGCGCAGGGGCAGCTGCTGCAGCGGGTG
CTGGCGCTTCCGGAGGGGATCC

FIGURE 5

KLHMTGGAGGYGRGAGAGAGAAAGAGAGAGGYGG
QGGYGAGAGAGAAAAGAGAGGAGGYGRGAGAGA
GAAAGAGAGAGGYGGQGGYGAGAGAGAAAAGAG
AGGAGGYGRGAGAGAGAAAGAGAGAGGYGGQGGY
GAGAGAGAAAAGAGAGGAGGYGRGAGAGAGAAA
GAGAGAGGYGGQGGYGAGAGAGAAAAGAGAGGA
GGYGRGAGAGAGAAAGAGAGAGGYGGQGGYGAGA
GAGAAAAGAGAGGAGGYGRGAGAGAGAAAGAGA
GAGGYGGQGGYGAGAGAGAAAAGAGAGGAGGYG
RGAGAGAGAAAGAGAGAGGYGGQGGYGAGAGAGA
AAAAGAGAGGAGGYGRGAGAGAGAAAGAGAGG
YGGQGGYGAGAGAGAAAAGAGASGGD

FIGURE 6

AAGCTT<u>CATATG</u>GGATCAACCGGT<u>CCCGGG</u>GGTCCGGGTGGTTATGGT
CCTGGTGGTAGTGGTCCAGGTGGCTATGGACCGGGTGGTTCCGGTCCA
GGCGGTTATGGCCCTGGCGGTTCAGGTCCGGGTGGATACGGACCAGGT
GGCAGCGGTCCGAGTGGTCCGGGTAGTGCAGCAGCAGCAGCCGCAGC
TGCAGGTCCAGGGGGATATGGTCCAGGGGGTAGCGGACCTGGCGGTT
ATGGGCCAGGTGGCTCTGGCCCTGGTGGATATGGCCCAGGCGGAAGTG
GCCCAGGTGGTTACGGACCTGGGGGATCAGGACCAGGCGGTTACGGT
CCGGGTGGCTCAGGTCCTAGCGGTCCGGGTTCAGCCGCAGCGGCAGCA
GCAGCGGCAGGACCGGGTGGCTATGGGCCAGGGGGTTCGGGACCTGG
TGGTTATGGACCTGGCGGAAGCGGTCCTGGGGGTTACGGTCCAGGTGG
AAGTGGACCGTCAGGTCCAGGTAGCGCAGCTGCCGCTGCAGCCGCAG
CAGGTCCAGGTGGGTACGGTCCTGGTGGTTCTGGACCGGGTGGGTATG
GTCCGGGTGGAAGCGGACCGGGTGGATATGGCCCTGGGGGATCTGGT
CCTGGCGGATATGGACCTGGTGGGTCGGGACCAGGGGGATACGGACC
GGGTGGTAGTGGCCCAGGCGGATACGGTCCTGGCGGTAGCGGTCCATC
AGGTCCGGGATCTGCTGCTGCTGCGGCAGCTGCAGCCGGACCAGGGG
GTTATGGACCAGGTGGTTCAGGACCAGGTGGCTACGGTCCAGGCGGTA
GTGGGCCTGGGGGATATGGTCCGGGTGGCTCTGGGCCTGGCGGTTACG
GACCTGGCGGTAGTGGACCGGGTGGTTATGGCCCAGGTGGCTCCGGTC
CGGGTGGGTATGGGCCAGGTGGATCTGGGCCAGGCGGTTATGGTCCAG
GGGGATCGGGTCCAGGTGGATATGGCCCAGGTGGTTCAGGTCCATCTG
GTCCGGGTTCCGCAGCTGCAGCCGCAGCCGCAGCTT<u>CCGGA</u>GGGCCCG
ATATCCTCGAG<u>GGATCC</u>

FIGURE 7

KLHMGSTGPGGPGGYGPGGSGPGGYGPGGSGPGGY
GPGGSGPGGYGPGGSGPSGPGSAAAAAAAAGPGGY
GPGGSGPGGYGPGGSGPGGYGPGGSGPGGYGPGGS
GPGGYGPGGSGPSGPGSAAAAAAAAGPGGYGPGGS
GPGGYGPGGSGPGGYGPGGSGPSGPGSAAAAAAAA
GPGGYGPGGSGPGGYGPGGSGPGGYGPGGSGPGGY
GPGGSGPGGYGPGGSGPGGYGPGGSGPSGPGSAAA
AAAAAGPGGYGPGGSGPGGYGPGGSGPGGYGPGGS
GPGGYGPGGSGPGGYGPGGSGPGGYGPGGSGPGGY
GPGGSGPGGYGPGGSGPSGPGSAAAAAAAASGGPDI
LEGS

FIGURE 8

AAGCTTCATATGACCGGTGGTTATCCGGGTGGCTATCCTGGTGGTCAG
GGTGCAGGTCCGCTGGGTGGTGTTCCGCTGGTTAGCCAGAGCCTGGAT
AATCTGGGTGGTGGTGGTGCACAGGCAGGTCTGATTAGCCGTGTTGCA
AATGCACTGGCAAATACCAGCACCCTGCGTGCAGTTCTGCGTCGTGGT
GTTAGCCAGAATACCGTTAATAATGTTGTTCAGCGTACCGTTCAGAGC
CTGGCCAATACCCTGGGTGTTGATGGTAATAATCTGGCACGTATTGCA
AGCCAGGCAATTAGCCAGGTTCCGGCAGGTAGCGATACCAATGCCTAT
GCACAGGCACTGAGCACCGCAAATCTGGTTACAGGTGGTATTCTGAAT
GAACGCAATATTGATAGCCTGGGTAGCCGTGTTCTGAGCGCAGTTCTG
AATGGTGTTAGCAGCGCAGCACAGGGTCTGGGTATTAATGTTGATACC
GGCAATCTGCAGGGTGATATTCGTAGCAGCACCGGCTTTCTGAGCACC
GGCAGCAGCAGCACCATTCTGAGCCAGACCGCAGCAAGCACCACCAG
TGGTGCAGAAAGCACCAGTGGCGGTTATCCTGGCGGTTACCCAGGCGG
ACAGGGTGCTGGACCGTTAGGTGGCGTGCCTCTGGTGAGCCCGTCACT
GGATAATTTAGGCGGTGGCGGTGCCCAAGCTGGCCTGATTTCACGTGT
TGCCAACGCCCTGGCGAATACGTCAACACTGCGTGCCGTGTTACGTCG
CGGTGTTTCACAGAATACAGTGAATAACGTGGTGCAGCGCACCGTGCA
GTCACTGGCAAACACCCTGGGCGTGGATGGCAACAATTTAGCCCGTAT
TGCATCACAGGCAATCTCTCAGGTTCCTGCCGGTTCAGATACAAATGC
ATACGCCCAGGCCCTGTCAACCGCCAATTTAGTGACGGGTGGCATTCT
GAACGAGCGTAACATTGATTCACTGGGTTCACGTGTTCTGTCAGCCGT
GCTGAATGGCGTTTCAAGTGCAGCCCAGGGTTTAGGCATTAACGTGGA
TACAGGTAACCTGCAGGGCGATATCCGTTCAAGCACAGGTTTTCTGAG
TACAGGTAGCAGTTCAACCATTCTGTCACAGACAGCAGCATCAACCAC
CTCAGGTGCAGAAACCTCCGGAGGGGATCC

FIGURE 9

KLHMTGGYPGGYPGGQGAGPLGGVPLVSQSLDNLG
GGGAQAGLISRVANALANTSTLRAVLRRGVSQNTV
NNVVQRTVQSLANTLGVDGNNLARIASQAISQVPAG
SDTNAYAQALSTANLVTGGILNERNIDSLGSRVLSA
VLNGVSSAAQGLGINVDTGNLQGDIRSSTGFLSTGS
SSTILSQTAASTTSGAESTSGGYPGGYPGGQGAGPL
GGVPLVSPSLDNLGGGGAQAGLISRVANALANTSTL
RAVLRRGVSQNTVNNVVQRTVQSLANTLGVDGNNL
ARIASQAISQVPAGSDTNAYAQALSTANLVTGGILN
ERNIDSLGSRVLSAVLNGVSSAAQGLGINVDTGNLQ
GDIRSSTGFLSTGSSSTILSQTAASTTSGAETSGGD

FIGURE 10

```
CCCGGGTGGCTATGGTCCTGGACAGCAAGGTCCTGGCGGTTACGGTCC
TGGCCAACAGGGTCCCTCTGGTCCAGGCAGTGCAGCTGCCGCAGCCGC
CGCAGCgGGTCCGGACCCGGGTGGCTATGGTCCTGGACAGCAAGGTCC
TGGCGGTTACGGTCCTGGCCAACAGGGTCCCTCTGGTCCAGGCAGTGC
AGCTGCCGCAGCCGCCGCAGCgGGTCCGGACCCGGGTGGCTATGGTCC
TGGACAGCAAGGTCCTGGCGGTTACGGTCCTGGCCAACAGGGTCCCTC
TGGTCCAGGCAGTGCAGCTGCCGCAGCCGCCGCAGCgGGTCCGGACCC
GGGTGGCTATGGTCCTGGACAGCAAGGTCCTGGCGGTTACGGTCCTGG
CCAACAGGGTCCCTCTGGTCCAGGCAGTGCAGCTGCCGCAGCCGCCGC
AGCgGGTCCGGACCCGGGTGGCTATGGTCCTGGACAGCAAGGTCCTGG
CGGTTACGGTCCTGGCCAACAGGGTCCCTCTGGTCCAGGCAGTGCAGC
TGCCGCAGCCGCCGCAGCgGGTCCGGACCCGGGTGGCTATGGTCCTGG
ACAGCAAGGTCCTGGCGGTTACGGTCCTGGCCAACAGGGTCCCTCTGG
TCCAGGCAGTGCAGCTGCCGCAGCCGCCGCAGCgGGTCCGGACCCGGG
TGGCTATGGTCCTGGACAGCAAGGTCCTGGCGGTTACGGTCCTGGCCA
ACAGGGTCCCTCTGGTCCAGGCAGTGCAGCTGCCGCAGCCGCCGCAGC
gGGTCCGGACCCGGGTGGCTATGGTCCTGGACAGCAAGGTCCTGGCGG
TTACGGTCCTGGCCAACAGGGTCCCTCTGGTCCAGGCAGTGCAGCTGC
CGCAGCCGCCGCAGCgGGTCCGGACCCGGGTGGCTATGGTCCTGGACA
GCAAGGTCCTGGCGGTTACGGTCCTGGCCAACAGGGTCCCTCTGGTCC
AGGCAGTGCAGCTGCCGCAGCCGCCGCAGCgGGTCCGGACCCGGGTGG
CTATGGTCCTGGACAGCAAGGTCCTGGCGGTTACGGTCCTGGCCAACA
GGGTCCCTCTGGTCCAGGCAGTGCAGCTGCCGCAGCCGCCGCAGCgGG
TCCGGACCCGGGTGGCTATGGTCCTGGACAGCAAGGTCCTGGCGGTTA
CGGTCCTGGCCAACAGGGTCCCTCTGGTCCAGGCAGTGCAGCTGCCGC
AGCCGCCGCAGCgGGTCCGGACCCGGGTGGCTATGGTCCTGGACAGCA
AGGTCCTGGCGGTTACGGTCCTGGCCAACAGGGTCCCTCTGGTCCAGG
CAGTGCAGCTGCCGCAGCCGCCGCAGCgGGTCCGGACCCGGGTGGCTA
TGGTCCTGGACAGCAAGGTCCTGGCGGTTACGGTCCTGGCCAACAGGG
TCCCTCTGGTCCAGGCAGTGCAGCTGCCGCAGCCGCCGCAGCgGGTCC
GGACCCGGGTGGCTATGGTCCTGGACAGCAAGGTCCTGGCGGTTACGG
TCCTGGCCAACAGGGTCCCTCTGGTCCAGGCAGTGCAGCTGCCGCAGC
CGCCGCAGCgGGTCCGGACCCGGGTGGCTATGGTCCTGGACAGCAAGG
TCCTGGCGGTTACGGTCCTGGCCAACAGGGTCCCTCTGGTCCAGGCAG
TGCAGCTGCCGCAGCCGCCGCAGCgGGTCCGGACCCGGGTGGCTATGG
TCCTGGACAGCAAGGTCCTGGCGGTTACGGTCCTGGCCAACAGGGTCC
CTCTGGTCCAGGCAGTGCAGCTGCCGCAGCCGCCGCAGCgGGTCCGGA
```

FIGURE 12 pET19-SX1A Composite
2525bp
AGCTTCTTTCGGGCTTTGTTAGCAGCCGGATCCTCGAGCATATGCTTGTCGTCGTCGTC
GATATGGCCGCTGCTGTGATGATGATGATGATGATGATGATGGCCCATGGTATATC
TCCTTCTTAAAGTTAAACAAAATTATTTCTAGAGGGGAATTGTTATCCGCTCACAATTC
CCCTATAGTGAGTCGTATTAATTTCGCGGGATCGAGATCTGACCTGTTATCGCACAATG
ATTCGGTTATACTGTTCGCCGTTGTCCAACAGGACCGCCTATAAAGGCCAAAAATTTTA
TTGTTAGCTGAGTCAGGAGATGCGGATGTTAAAGCGTGAAATGAACATTGCCGATTATG
ATGCCGAACTGTGGCAGGCTATGGAGCAGGAAAAAGTACGTCAGGAAGAGCACATCGAA
CTGATCGCCTCCGAAAACTACACCAGCCCGCGCGTAATGCAGGCGCAGGGTTCTCAGCT
GACCAACAAATATGCTGAAGGTTATCCGGGCAAACGCTACTACGGCGGTTGCGAGTATG
TTGATATCGTTGAACAACTGGCGATCGATCGTGCGAAAGAACTGTTCGGCGCTGACTAC
GCTAACGTCCAGCCGCACTCCGGCTCCCAGGCTAACTTTGCGGTCTACACCGCGCTGCT
GGAACCAGGTGATACCGTTCTGGGTATGAACCTGGCGCATGGCGGTCACCTGACTCACG
GTTCTCCGGTTAACTTCTCCGGTAAACTGTACAACATCGTTCCTTACGGTATTGATGCT
SHMT ACCGGTCATATCGACTACGCCGATCTGGAAAAACAAGCCAAAGAACACAAGCCGAAAAT
GATTATCGGTGGTTTCTCTGCATATTCCGGCGTGGTGGACTGGGCGAAAATGCGTGAAA
TCGCTGACAGCATCGGTGCTTACCTGTTCGTTGATATGGCGCACGTTGCGGGCCTGGTT
GCTGCTGGCGTCTACCCGAACCCGGTTCCTCATGCTCACGTTGTTACTACCACCACTCA
CAAAACCCTGGCGGGTCCGCGCGGCGGCCTGATCCTGGCGAAAGGTGGTAGCGAAGAGC
TGTACAAAAAACTGAACTCTGCCGTTTTCCCTGGTGGTCAGGGCGGTCCGTTGATGCAC
GTAATCGCCGGTAAAGCGGTTGCTCTGAAAGAAGCGATGGAGCCTGAGTTCAAAACTTA
CCAGCAGCAGGTCGCGAAAAACGCTAAAGCGATGGTAGAAGTGTTCCTCGAGCGCGGCT
ACAAAGTGGTTTCCGGCGGCACTGATAACCACCTGTTCCTGGTTGATCTGGTTGATAAA
AACCTGACCGGTAAAGAAGCAGACGCCGCTCTGGGCCGTGCTAACATCACCGTCAACAA
AAACAGCGTACCGAACGATCCGAAGAGCCCGTTTGTGACCTCCGGTATTCGCGTGGGTA
CTCCGGCAATTACGCGTCGCGGCTTCAAAGAAGCAGAAGCGAAAGAACTGGCTGGCTGG
ATGTGTGACGTGCTGGACAGCATCAATGATGAAGCCGTTATCGAGCGCATCAAAGGTAA
AGTTCTCGACATCTGCGCACGTTACCCGGTTTACGCATAAGCGAAACGGTGATTTGCTG
ACAATGTGCTCGTTGTTCATGTTGGATGCGGCATGAACACGTCGACGTAGCCCGAGAC
GATAAGTTCGCTTACCGGCTCGAATGAAGAGAGCTTCTCTCGATATTCAGTGCAGAATG
AAAATCAGGTAGCCGAGTTCCAGGATGCGGGCATCGTATAATGGCTATTACCTCAGCCT
GlyT TCCAAGCTGATGATGCGGGTTCGATTCCCGCTGCCCGCTCCAAGATGTGCTGATATAGC
TCAGTTGGTAGAGCGCACCCTTGGTAAGGGTGAGGTCGGCAGTTCGAATCTGCCTATCA
GCACCACTTCTTTTCTCCTCCCTGTTTTTTCCTTCTGTTTATTGCATTCAACAAGTCGG
GCATGTTGCAAGCTTCTTGCAATCGGTGTGGAAAACGGTAGTATTAGCAGCCACGAGTC
GGCACGTAGCGCAGCCTGGTAGCGCACCGTCATGGGGTGTCGGGGGTCGGAGGTTCAAA
ProL TCCTCTCGTGCCGACCAAAAATCCCAAGAAAAAACCAACCCTTACGGTTGGTTTTTTTA
TATCTGCAATTAATTCGATAAACAGACCGTGACACATCACGAATTCCTCGCACCACGAC
TTTAAAGAATTGAACTAAAAATTCAAAAAGCAGTATTTCGGCGAGTAGCGCAGCTTGGT
ProM AGCGCAACTGGTTTGGGACCAGTGGGTCGGAGGTTCGAATCCTCTCTCGCCGACCAATT
TTGAACCCCGCTTCGGCGGGTTTTTGTTTCTGTGCATTTCGTCACTTTCCCGCATG
CACCATTCCTTGCGGCGGCGGTGCTCAACGGCCTCAACCTACTACTGGGCTGCTTCCTA
ATGCAGGAGTCGCATAAGGGAGAGCGTCGAGATCCCGGACACCATCGAATGGCGCAAAA
CCTTTCGCGGTATGGCATGATAGCGCCCGGAAGAGAGTCAATTCAGG

FIGURE 16

| | | | | | | | | | | | | |
|---|---|---|---|---|---|---|---|---|---|---|---|---|
| G | G | Y | G | P | G | A | G | Q | Q | G | P | G | S |
| GGT | GGA | TAT | GGT | CCT | GGA | GCA | GGT | CAA | CAA | GGA | CCA | GGT | AGT |
| Q | G | P | G | S | G | G | Q | Q | G | P | G | G | Q |
| CAA | GGA | CCT | GGT | TCT | GGA | GGT | CAA | CAA | GGA | CCA | GGT | GGA | CAA |
| G | G | Y | G | P | G | A | G | Q | Q | G | P | G | S |
| GGT | GGA | TAT | GGT | CCT | GGA | GCA | GGT | CAA | CAA | GGA | CCA | GGT | AGT |
| Q | G | P | G | S | G | G | Q | Q | G | P | G | G | Q |
| CAA | GGA | CCT | GGT | TCT | GGA | GGT | CAA | CAA | GGA | CAA | GGT | GGA | CAA |
| G | P | Y | G | P | S | A | A | A | A | A | A | | |
| GGT | CCT | TAT | GGA | CCA | AGT | GCA | GCA | GCA | GCA | GCA | GCA | | |

FIGURE 19

```
                    Promoter
CGTATTGACGTAAGGCGTAAAAGTGGTAGAATGCGCCTCCGCGGGAATAGCTCAG
                Glycine(G)GCC (GGT codon)
TTGGTAGAGCACGACCTTGCCAAGGTCGGGGTCGCGAGTTCGAGTCTCGTTTCCC
         Terminator                     Promoter
GCTCCAAATTTCCAACCCTCGCGTATTGACGTAAGGCGTAAAAGTGGTAGAATGC
                        Glutamine(Q) TTG (CAA codon)
GCCTCCTGGGGTATCGCCAAGCGGTAAGGCACCGGTTTTTGATACCGGCATTCCC
                         Terminator
TGGTTCGAATCCAGGTACCCCAGCCAAATTTCCAACCCTCGCGTATTGACGTAAG
       Promoter
GCGTAAAAGTGGTAGAATGCGCCTCCCGGCACGTAGCGCAGCCTGGTAGCGCACC
Proline(P) GGG (CCT codon)                      Terminator
GTCATGGGTGTCGGGGTCGGAGGTTCAAATCCTCTCGTGCCGACCAAATTTCC
                    Promoter
AACCCTCGCGTATTGACGTAAGGCGTAAAAGTGGTAGAATGCGCCTCCGGGCTA
                Alanine(A) TGC (GCA codon)
TAGCTCAGCTGGGAGAGCGCCTGCTTTGCACGCAGGAGGTCTGCGGTTCGATCCC
            Terminator                   Promoter
GCATAGCTCCACCAAATTTCCAACCCTCGCGTATTGACGTAAGGCGTAAAAGTGG TAGAATGCGCCTCCGGTGAGGTGGCCGAGAGGCTGAAGGCGCTCCCCTGCTAAGG
                Serine(S) GCT (AGT codon)
GAGTATGCGGTCAAAAGCTGCATCCGGGGTTCGAATCCCCGCCTCACCGCCAAAT
Terminator              Promoter
TTCCAACCCTCGCGTATTGACGTAAGGCGTAAAAGTGGTAGAATGCGCCTCCGGT
                Tyrosine(Y) GTA (TAT codon)
GGGGTTCCCGAGCGGCCAAAGGGAGCAGACTGTAAATCTGCCGTCACAGACTTCG
                         Terminator
AAGGTTCGAATCCTTCCCCCACCACCAAATTTCCAACCCTCG
```

FIGURE 20

```
                  Promoter
CGTATTGACGTAAGGCGTAAAAGTGGTAGAATGCGCCTCCGCGGGCATCGTATAA
          Glycine(G) TCC (GGA codon)
TGGCTATTACCTCAGCCTTCCAAGCTGATGATGCGGGTTCGATTCCCGCTGCCCG
      Terminator                    Promoter
CTCCAAATTTCCAACCCTCGCGTATTGACGTAAGGCGTAAAAGTGGTAGAATGCG
          Proline(P) TGG (CCA codon)
CCTCCCGGCGAGTAGCGCAGCTTGGTAGCGCAACTGGTTTGGGACCAGTGGGTCG
                             Terminator
GAGGTTCGAATCCTCTCTCGCCGACCAAATTTCCAACCCTCGCGTATTGACGTAA
Promoter
GGCGTAAAAGTGGTAGAATGCGCCTCCGGTGAGGTGTCCGAGTGGCTGAAGGAGC
          Serine(S) GGA (TCT codon)
ACGCCTGGAAAGTGTGTATACGGCAACGTATCGGGGGTTCGAATCCCCCCCTCAC
       Terminator                   Promoter
CGCCAAATTTCCAACCCTCGCGTATTGACGTAAGGCGTAAAAGTGGTAGAATGCG
          Threonine(T) GGT (ACT codon)
CCTCCGCTGATATGGCTCAGTTGGTAGAGCGCACCCTTGGTAAGGGTGAGGTCCC
                             Terminator
CAGTTCGACTCTGGGTATCAGCACCAAATTTCCAACCCTCGCGTATTGACGTAAG
Promoter
GCGTAAAAGTGGTAGAATGCGCCTCCGCGTTGTTAGCTCAGCCGGACAGAGCAAT
      Arginine(R) TCT (AGA codon)
TGCCTTCTGAGCAATCGGtCACTGGTTCGAATCCAGTACAACGCGCCAAATTTCC
Terminator
AACCCTCG
```

FIGURE 21

EXPRESSION SYSTEMS AND METHODS OF PRODUCING SPIDER SILK PROTEINS

RELATED APPLICATIONS

This application claims priority to U.S. Provisional Patent Application No. 61/707,571, filed Sep. 28, 2012, the entirety of which is herein incorporated by reference.

TECHNICAL FIELD

The present disclosure relates to the field of molecular biology. More specifically it relates to the field of spider silk protein upregulation.

BACKGROUND

Protein upregulation is a molecular biology technique used for the production of large amounts of protein in a host organism. Proteins produced by upregulation may be used in a variety of products that improve human health and well-being. Often, proteins are chosen for upregulation based on properties that may provide for products with desired material characteristics or performance. Generally, proteins comprise at least one polypeptide chain. Polypeptides are amino acid chains, or sequences, linked by peptide bonds. The term protein may refer to a polypeptide chain after folding, interaction with other polypeptide chains, or the addition of other parts such as carbohydrates, lipids, or signal sequences, that make the protein a functional biological product of translation.

Spider silk is known to outperform many synthetic fibers in terms of material characteristics. Spider silk is made up of spider silk proteins that have unique mechanical properties, including strength, density, extensibility, toughness, and others.

Despite advances and existing systems for protein upregulation, attempts at upregulation for spider silk proteins have been hampered. One attempt at spider silk protein upregulation is described in Brooks et al., Properties of synthetic spider silk fibers based on *Argiope aurantia* MaSp2. Biomacromolecules 9:1506-1510 (2008), which is hereby incorporated by reference in its entirety.

SUMMARY

The present disclosure in aspects and embodiments addresses these various needs and problems by providing an expression system useful in the upregulation of spider silk protein expression, comprising a host cell, a synthetic spider silk polypeptide-encoding nucleotide sequence, and a nucleotide sequence selected from the group consisting of at least one synthetic tRNA molecule-encoding nucleotide sequence, and a synthetic serine hydroxymethyl transferase (SHMT)-encoding nucleotide sequence.

In embodiments, the expression system comprises the at least one synthetic tRNA molecule-encoding nucleotide sequence.

In related embodiments, the at least one synthetic tRNA molecule-encoding nucleotide sequence when expressed is a tRNA that binds to an amino acid selected from the group consisting of glycine, glutamine, proline, alanine, serine, and tyrosine.

In some embodiments, the expression system comprises the synthetic SHMT-encoding nucleotide sequence.

In certain embodiments, the expression system comprises the at least one synthetic tRNA molecule-encoding nucleotide sequence, and the synthetic SHMT-encoding nucleotide sequence.

In some embodiments, the synthetic nucleotide sequences are provided on at least one vector.

In embodiments, the host cell is an *E. coli* cell.

In some embodiments, the synthetic spider silk polypeptide-encoding nucleotide sequence encodes for spider silk proteins selected from the group consisting of MaSP1, MaSP2, MiSP, MiSp2, AcSP, FLYS, FLAS, and piriform.

In certain embodiments, the synthetic spider silk polypeptide-encoding nucleotide sequence encodes for at least one polypeptide sequence selected from the group consisting of SEQ ID NO:2, SEQ ID NO:4, SEQ ID NO:6, SEQ ID NO:8, SEQ ID NO:10, SEQ ID NO:12, SEQ ID NO:13, and SEQ ID NO:14.

In some embodiments, the nucleotide sequences encoding the at least one polypeptide sequence are sequentially arranged and provide for a single recombinant spider silk polypeptide.

In some embodiments, the synthetic spider silk polypeptide-encoding nucleotide sequence has a GC % that corresponds to the GC % of the host cell.

In some embodiments, the GC % of the synthetic spider silk polypeptide-encoding nucleotide sequence is within 15 percentage points of the GC % of the host cell.

In some embodiments, the at least one synthetic tRNA molecule-encoding nucleotide sequence encodes a tRNA having an anticodon that corresponds to a codon provided in a synthetic spider silk polypeptide-encoding nucleotide sequence.

In embodiments, the present invention relates to methods of upregulating synthetic spider silk polypeptide production in a host cell, the method comprising:
providing in the host cell a synthetic spider silk polypeptide-encoding nucleotide sequence, and
providing in the host cell:
at least one synthetic tRNA molecule-encoding nucleotide sequence, or
a synthetic SHMT-encoding nucleotide sequence.

In some embodiments of the methods, at least one synthetic tRNA molecule-encoding nucleotide sequence is provided.

In some embodiments of the methods, the synthetic SHMT-encoding nucleotide sequence is provided.

In certain embodiments of the methods, at least one synthetic tRNA molecule-encoding nucleotide sequence and the synthetic SHMT-encoding nucleotide sequence are provided.

In embodiments of the methods, the synthetic spider silk polypeptide-encoding nucleotide sequence has a GC % that corresponds to the GC % of the host cell.

In some embodiments of the methods, the GC % of the synthetic spider silk polypeptide-encoding nucleotide sequence is within 15 percentage points of the GC % of the host cell.

In certain embodiments of the methods, the at least one synthetic tRNA molecule-encoding nucleotide sequence provides for a tRNA molecule having a anticodon that corresponds to a codon provided in a synthetic spider silk polypeptide-encoding nucleotide sequence.

The present disclosure also provides methods of upregulating synthetic spider silk polypeptide production in a host cell, comprising, providing in the host cell a synthetic spider silk polypeptide-encoding nucleotide sequence, and also providing in the host cell (i) at least one synthetic tRNA molecule-encoding nucleotide sequence, or (ii) a synthetic SHMT-encoding nucleotide sequence.

BRIEF DESCRIPTION OF THE DRAWINGS

FIG. 1 depicts features of the DNA sequence SEQ ID NO:1 that encodes the MaSP1 amino acid sequence SEQ ID NO:2 shown in FIG. 2.

FIG. 2 depicts an exemplary MaSP1 amino acid sequence SEQ ID NO:2.

FIG. 3 depicts features of a DNA sequence SEQ ID NO:3 that encodes the MaSP1 amino acid sequence SEQ ID NO:4 shown in FIG. 4.

FIG. 4 depicts an exemplary MaSP2 amino acid sequence SEQ ID NO:4.

FIG. 5 depicts features of a DNA sequence SEQ ID NO:5 that encodes the MiSP amino acid sequence SEQ ID NO:6 shown in FIG. 6.

FIG. 6 depicts an exemplary MiSP amino acid sequence SEQ ID NO:6.

FIG. 7 depicts features of a DNA sequence SEQ ID NO:7 that encodes the FLYS amino acid sequence SEQ ID NO:8 shown in FIG. 8.

FIG. 8 depicts an exemplary FLYS amino acid sequence SEQ ID NO:8.

FIG. 9 depicts features for a DNA sequence SEQ ID NO:9 that encodes the ACSP amino acid sequence SEQ ID NO:10 shown in FIG. 10.

FIG. 10 depicts an exemplary ACSP amino acid sequence SEQ ID NO:10.

FIG. 11 depicts features of an expression vector having a DNA sequence SEQ ID NO:11 encoding the recombinant spider silk amino acid sequence SEQ ID NO:12 shown in FIG. 12.

FIG. 12 depicts an exemplary MaSP2 amino acid sequence SEQ ID NO:12.

FIG. 16 depicts SEQ ID NO:23 from a pET19-SX (Kan) expression vector for upregulating the production of synthetic spider silk polypeptides.

FIG. 19 depicts an exemplary nucleotide SEQ ID NO:17 and amino acid sequence SEQ ID NO:13 for a balanced tRNA approach to upregulating polypeptide expression.

FIG. 20 depicts a DNA construct that provides a recombinant nucleotide sequence SEQ ID NO:21 encoding six tRNAs for increased spider silk expression.

FIG. 21 depicts a DNA construct having the sequence SEQ ID NO:22 that provides tRNAs for the glycine, proline, and serine amino acids.

DETAILED DESCRIPTION

Figure 13:
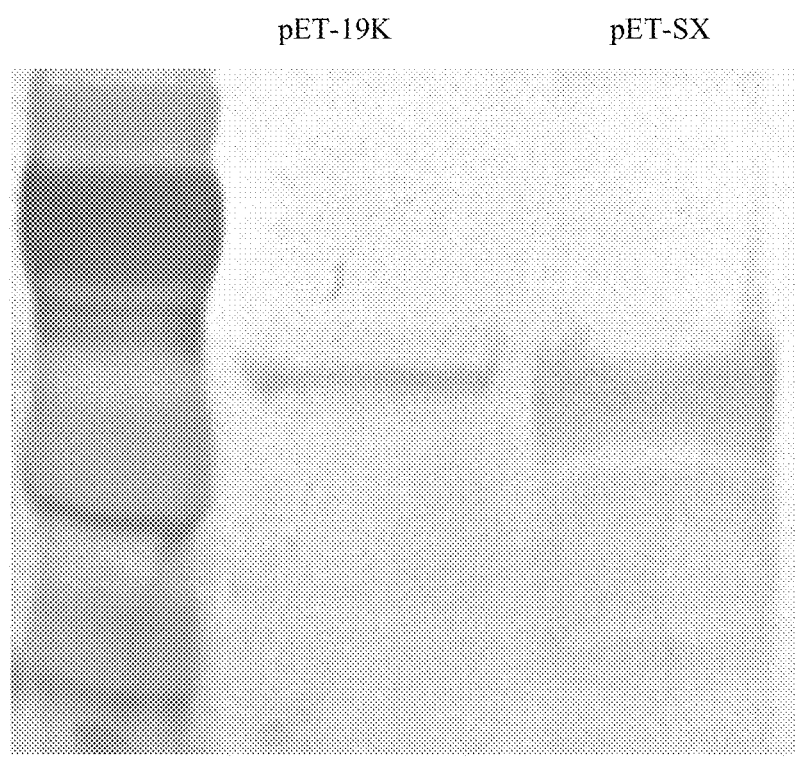
FIG. 13 depicts the expression of MaSP1 from pET-19 and pET-SX.

The present disclosure identifies the need for a reliable expression system for the upregulation of spider silk proteins. To develop such an expression system, this disclosure further identifies certain characteristics of spider silk polypeptides and of the genes that encode them, that have hampered prior attempts to upregulate spider silk proteins/polypeptides in genetically engineered hosts, including *E. coli*. These characteristics include the use of six primary amino acids, a high demand for glycine, and high GC % of the genes encoding the proteins. These features can make protein production difficult in host cells that may not have sufficient tRNA molecules to carry out upregulation of synthetic spider silk polypeptides and proteins.

For example, native *E. coli* genetic machinery is not optimized for DNA sequences of high GC % when making mRNA and, thus, the amounts of spider silk mRNA produced from conventional spider silk nucleotide sequences in *E. coli* cells may be limited. For instance, the native codon usage profile of *Argiope auran*, a common garden spider, is different from *E. coli*'s native codon usage. The GC % of the DNA molecule from the spider (GC=75%) is significantly different from the average GC % of native *E. coli* genes (GC=51%). In addition, *E. coli* may have insufficient levels of glycine present for the upregulation of spider silk proteins.

Accordingly, the present disclosure overcomes the various limitations described above by providing methods, compositions, reagents, and kits related to expression systems, expression vectors, and recombinant nucleotide sequences useful in the production of synthetic spider silk proteins from a genetically engineered host cell. The present disclosure also provides for a genetically engineered host cell for the production of spider silk proteins.

In the following description, numerous specific details are provided for a thorough understanding of specific preferred embodiments. However, those skilled in the art will recognize that embodiments can be practiced without one or more of the specific details, or with other methods, components, materials, etc. In some cases, well-known structures, materials, or operations are not shown or described in detail to avoid obscuring aspects of the preferred embodiments. Furthermore, the described features, structures, or characteristics may be combined in any suitable manner in a variety of alternative embodiments. Thus, the following more detailed description of the embodiments is not intended to limit the scope of the invention, but is merely representative of the various embodiments of the invention.

DEFINITIONS

As used herein, "synthetic" means to form by using, at least in part, a non-naturally occurring composition or biological process. By way of example, a "synthetic spider silk protein" may be produced using non-naturally occurring nucleotide sequences, genetically engineered cells, or methods guided by the hand of man.

As used herein, "host cell" includes any cell type that is susceptible to transformation, transfection, or transduction, with a nucleic acid construct or vector.

As used herein, "GC %" means percent content of a DNA sequence that is composed of guanine (G) and cytosine (C) nucleotides.

As used herein, "select codon usage" means the inclusion of at least one codon that has been selected for a property, in a non-naturally occurring nucleotide sequence. For example, a codon may be selected for its GC %, or because it corresponds to tRNAs available in a host cell, or for any other desirable characteristic. Generally, select codon usage is used to provide a modified nucleic acid sequence that encodes a spider silk polypeptide, and is a component of a spider silk expression system useful for the overproduction of spider silk proteins.

As used herein, the phrase "balanced tRNA" means providing multiple tRNAs for at least one amino acid type to be incorporated into a protein to be expressed in an expression system of the present invention.

As used herein, the phrase "fewest tRNA" means providing only one exogenous tRNA for each amino acid type in a protein to be expressed in an expression system of the present invention.

As used herein, the term "protein sequence" means a polypeptide sequence of amino acids that is the primary structure of a protein.

As used herein, "modification" may include any type of alteration to a nucleotide sequence or protein sequence related to the present invention. Modifications include, but are not limited to, a substitution, a deletion, and/or additions.

As used herein, "control sequence" means a component that regulates the expression of a nucleic acid sequence of the present invention. A control sequence may be either native or foreign to the nucleotide sequence. Control sequences include, but are not limited to, a leader, polyadenylation site, propetide sequence, promoter, signal peptide sequence, and transcription terminator.

As used herein, "operatively linked" denotes a configuration in which a control sequence is positioned at a position relative to the coding sequence of a nucleotide sequence such that the control sequence directs the expression of the coding sequence of the nucleotide sequence.

As used herein, "expression" refers to the production of a protein or polypeptide related to the present disclosure.

As used herein, "vector" means an expression vector that is a linear or circular DNA molecule that comprises a nucleic acid sequence that is operably linked to control sequence.

In this specification and the claims that follow, singular forms such as "a," "an," and "the" include plural forms unless the content clearly dictates otherwise. All ranges disclosed herein include, unless specifically indicated, all endpoints and intermediate values. In addition, "optional" or "optionally" refer, for example, to instances in which subsequently described circumstance may or may not occur, and include instances in which the circumstance occurs and instances in which the circumstance does not occur. The terms "one or more" and "at least one" refer, for example, to instances in which one of the subsequently described circumstances occurs, and to instances in which more than one of the subsequently described circumstances occurs.

I. Host Cells

Any host cell capable of spider silk protein expression may be used. Suitable host cells include bacteria, yeast, insect, and mammalian cells. Examples of bacterial cells that may be used include E. coli. In some embodiments, the E. coli may be E. coli K-12, DH5α or BL21 (DE3).

Recombinant nucleotide sequences that encode for expression system components may be provided on expression vectors, as described below. Alternatively, the recombinant nucleotide sequences encoding for expression system components may be integrated into the bacterial genome. Integration of recombinant sequences into a host cell's genome may be done by any number of methods standard in the field of molecular biology. For example, homologous recombination may be used to integrate nucleotide sequences into a host cell's genome.

II. Vectors

Any suitable vector capable of protein, polypeptide, or tRNA expression may be used in the expressions systems. In embodiments, the vector may be a plasmid encoding components of a spider silk expression system, including one or more spider silk proteins, one or more desired tRNAs, SHMT, other desired marker proteins or tags, or a combination thereof. In embodiments, multiple vectors may be employed to provide the desired components.

In embodiments, suitable vectors may include an expression cassette. Expression cassettes may include at least one control sequence and at least one coding sequence for the desired component. For example, the expression cassette may include, at least one promoter sequence, one coding sequence for the desired polypeptide, and at least one terminator sequence. In some examples, a promoter sequence may precede and be operatively linked to a series of nucleotide sequences that encode spider silk protein sequences. Alternatively, multiple promoters may be used. A promoter may precede each spider silk sequences in a series of spider silk sequences. Vectors may also include a His-tag, GFP, or at least one terminator sequence. In some embodiments with multiple promoters preceding each component coding sequence in a series of sequences, it may be preferable to provide a His-tag, GFP, or terminator sequence, for each component sequence in the series.

Recombinant nucleotide sequences may comprise promoters that match or correspond to the host cell type, use the t-RNAs and codons that fit the preferences of that particular host cell type and utilize plasmids for that host cell type for transfection and transformation.

Exemplary expression vectors include pET-SX, pSB1C3, pSB3K3, pSB1K3, pSB1A3, pET19 and its derivatives, pUC18 and its derivatives.

In some embodiments, the expression vector may be based on the pET-19 vector, but differs in that it 1) has kanamycin resistance, 2) contains a DNA sequence that results in the expression of SHMT that converts the amino acid serine to glycine and 3) contains DNA sequences that produce additional tRNAs for glycine, alanine and proline (the 3 most prevalent amino acids in spider silk). Such a vector may be utilized to increase expression of existing rSSP's that are high in glycine, alanine and proline or it can be used to express optimized recombinant spider silk genes as described below. Such a vector is herein described as pET-SX.

III. Spider Silk Proteins

Suitable spider silk proteins include those encoded by naturally occurring nucleic acid sequences or synthetic nucleic acid sequences. Synthetic sequences include modified, recombinant, and engineered sequences. Exemplary spider silk proteins include MaSP1, MaSP2, MiSP, MiSp2, AcSP, FLYS, FLAS, and piriform the abbreviations of which are described below. Spider silk proteins may comprise one or more of the polypeptide sequences described herein.

MaSP1: Dragline silk is comprised of two unique proteins that contribute to the remarkable mechanical properties of the silk. This is one of those two proteins with the other being MaSP2. MaSP1 is characterized by glycine-alanine repeats as well as there being no proline present in the protein sequence. An exemplary MaSP1 amino acid sequence is illustrated in FIG. 2 and set forth in SEQ ID NO:2.

Figure 12:
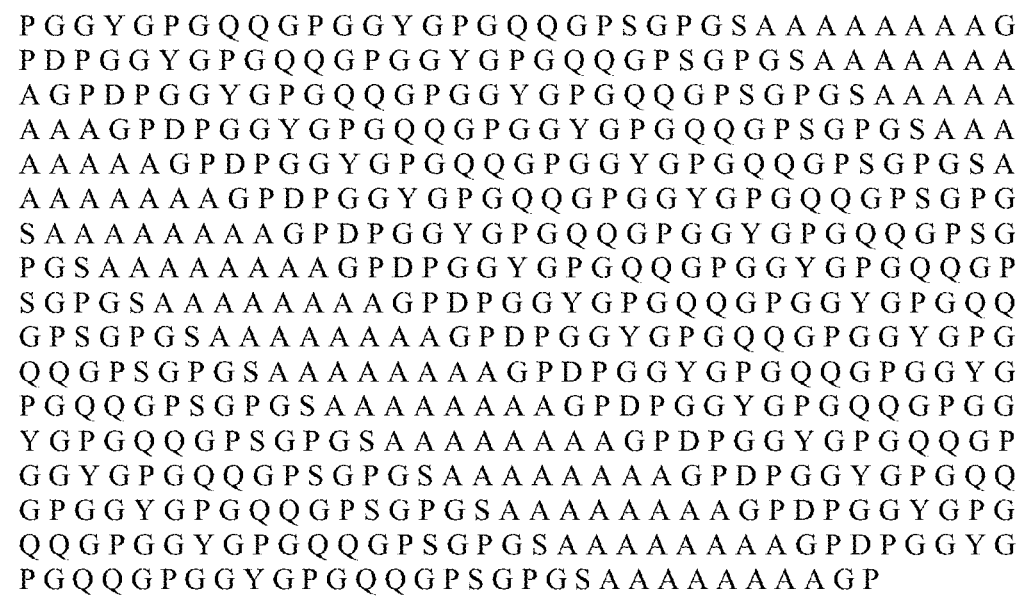

MaSP2: Dragline silk is comprised of two unique proteins that contribute to the remarkable mechanical properties of the silk. This is one of those two proteins with the other being MaSP1 (above). MaSP1 is characterized by poly-alanine repeats as well as proline present in the protein sequence. Exemplary MaSP2 amino acid sequences are illustrated in FIGS. 4, 12, and 19 and set forth in SEQ ID NO:4, SEQ ID NO:12, and SEQ ID NO: 13.

MiSP: Minor ampullate silk provides the auxiliary spiral for the web of orb weaving spiders. The mechanical properties of minor ampullate generally are that it is less extensible and non-elastic when compared to dragline silk. The native sequence is characterized by GGX and GA repeats separated by serine rich spacer regions. MiSP is also characterized as having two genes that encode for the protein, MiSP1 and MiSP2. The genes are very similar only differing in a substitution of serine for alanine in one codon of the repetitive portion of the gene. In examples, only one MiSP gene was constructed; however, any MiSP construct derived from MSP1, MSP2, or a combination thereof may be used. An exemplary MiSP amino acid sequence is illustrated in FIG. 6 and set forth in SEQ ID NO:6.

AcSP: Aciniform silk protein is the silk protein fiber used to swath prey once captured in the web and it also provides a cushion inside of cocoons for eggs. The fiber is comprised of a single protein. An exemplary AcSP amino acid sequence is illustrated in FIG. 10 and set forth in SEQ ID NO:10.

FLYS: This is a flagelliform-like sequence. Flagelliform is about 300% elastic and is used for the capture spiral on the web so as to absorb the impact of an insect. The repetitive portion of flagelliform that confers elasticity is a repeat of GPGGX where X can be alanine (A), tyrosine (Y) or serine (S). FLYS infers that tyrosine (Y) is in the X position of this repeat. FLYS is also a chimeric sequence as it also contains the MaSP2 poly-alanine repetitive region. Poly-alanine in known to confer strength forming β-sheets to the resulting fiber. This is a spider silk sequence not found in nature. An exemplary FLYS amino acid sequence is illustrated in FIG. 8 and set forth in SEQ ID NO:8.

FLAS: This is a flagelliform like sequence. Flegelliform is roughly 300% elastic and is used for the capture spiral on the web so as to absorb the impact of an insect. The repetitive portion of flagelliform that confers elasticity is a repeat of GPGGX where X can be alanine (A), tyrosine (Y) or serine (S). FLAS infers that alanine (A) is in the X position of this repeat, thereby resulting in the sequence KLHMGSTG-PGGPGGAGPGGAGPGGAGPGGAGPGGAGPGGAGP-GGAGPGGAGSGPGSAAAAAAAAGPGGAGPGGAG-PGGAGPGGAGPGGAGPGGAGPGGAGPGGAGPGGA-GPGGAGPSGPGSAAAAAAAAGPGGAGPGGAGPGG-AGPGGAGPGGAGPGGAGPSGPGSAAAAAAAAGPG-GAGPGGAGPGGAGPGGAGPGGAGPGGAGPGGAGP-GGAGPGGAGPGGAGPGGAGPGGAGPSGPGSAAAA-AAAAGPGGAGPGGAGPGGAGPGGAGPGGAGPGGA-GPGGAGPGGAGPGGAGPGGAGPGGAGPGGAGPGG-AGPGGAGPGGAGPGGAGPSGPGSAAAAAAAASGG-PDILEGS (SEQ ID NO: 27). FLAS is also a chimeric sequence as it also contains the MaSP2 poly-alanine repetitive region. Poly-alanine is known to confer strength forming β-sheets to the resulting fiber. This is a spider silk sequence not found in nature.

Piriform: Piriform is the silk protein spiders use as "attachment disks," to anchor their lines, and is probably one of the earliest evolved spider silks.

In addition, any recombinant spider silk protein or polypeptide capable of being produced bacterially may be used in the systems and methods described herein.

In embodiments, modification to the nucleic acid sequences that encode for spider silk proteins, contributes to the upregulation of spider silk protein in the host cell.

In embodiments, longer recombinant nucleotide sequences that encode for spider silk proteins may be generated by sequential arrangement of shorter spider silk protein encoding units, to provide for spider silk proteins with polypeptide sequences of a desired length. The nucleotide units may be sequentially added to a single coding sequence within a vector. The nucleotide units may be either the same or different units of coding sequence. Vectors having one or more nucleic acid sequences that encode spider silk proteins may have the sequences arranged in any manner that allows for the production of spider silk proteins. By way of example, multiple spider silk proteins may be oriented head-to-tail. Sets of nucleic acid sequences that encode at least one specific spider silk proteins may be combined into spider silk protein encoding units that can be sequentially incorporated into a vector backbone. For example, to produce a MaSP2 protein, various combinations of the nucleotide sequences encoding for the amino acid sequences SEQ ID NO:4, SEQ ID NO:12, and SEQ ID NO:13, may be ligated sequentially in a vector. Alternatively, any of the spider silk protein encoding nucleotide sequences provided herein may be sequentially arranged on a vector to provide a desired spider silk amino acid sequence.

IV. Upregulation

Various methods of upregulation that may be used alone or in any combination.

A. tRNAs

In embodiments, expression systems for up-regulating protein production may include a nucleic acid sequence that encodes for at least one supplemental tRNA having an anticodon that binds to at least one codon that specifies an amino acid component of a spider silk protein. Generally, amino acid components of a spider silk protein include glycine (G), glutamine (Q), proline (P), alanine (A), serine (S) and tyrosine (Y). Any desired combination of tRNAs may be used.

In some embodiments, multiple copies of a sequence encoding a tRNA specifying a particular amino acid component of a targeted/desired spider silk protein may be used. In related embodiments, tRNAs with different anticodons, which specify the same amino acid, may also be used. Nucleic acid sequences for tRNAs may be provided on the same vector that provides a spider silk protein sequence. Alternatively, nucleic acid sequences for tRNAs may be provided on a separate vector or vectors. As described above, recombinant nucleotide sequences that encode for tRNAs may be operably linked to a promoter and may be followed by a terminator sequence. In embodiments, the number of particular tRNAs may be varied.

In some embodiments, certain codon/anticodon base-pairings may include a wobble pairing at the $3^{rd}$ nucleotide in a codon, which is commonly referred to as the wobble position.

For example, one such tRNA molecule for the amino acid proline could have an anticodon UGG which compliments the mRNA codon CCA.

B. SHMT

In embodiments, expression systems for up-regulating protein production may include an exogenous nucleotide sequence that encodes for an enzyme to increase the availability of a desired amino acid to the host cell. For example, SHMT may be used to provide glycine. SHMT is an enzyme that functions in cellular one-carbon pathways by catalyzing the reversible, simultaneous conversions of L-serine to glycine. Host cells, including *E. coli*, may have endogenous versions of this enzyme; however, the levels of glycine provided by the endogenous SHMT may be insufficient for the upregulation of spider silk proteins in the host cells. The exogenous nucleotide sequence that encodes for at least one SHMT provides for an expression system with high levels of SHMT that contribute to the upregulation of spider silk proteins in the host cell. In some embodiments, nucleotide sequences encoding SHMT may be provided on a vector that also provides for recombinant spider silk proteins or tRNAs. Alternatively, SHMT may be provided on a different vector.

C. Select Codon Usage

In embodiments, expression systems for up-regulating protein production may include modified nucleotide sequences designed to correspond with a host cell's tRNA pool or GC %.

Examples of spider silk amino acid sequences generated from modified DNA sequences are provided in SEQ ID NO:13 and SEQ ID NO:14. The unmodified DNA sequences and corresponding modified sequences are provided in SEQ ID NOs:15-20.

In some embodiments, nucleotide sequences encoding synthetic spider silk protein polypeptides are modified to correspond with the host cell tRNA pool.

In some embodiments, modified nucleotide sequences that encode spider silk protein polypeptides may be constructed using select codon usage. Select codon usage may provide for nucleotide sequences (encoding desired amino acid sequences or tRNA molecules) having a GC % that correspond to the GC % of the host genome. Select codon usage may be achieved by replacing codons in a targeted nucleotide sequence with codons that have a GC % closer to the GC % of the host cell than is provided in the targeted sequence. Any codon modification that brings the GC % of the target sequence and the host genome in closer correspondence that would otherwise exist may be employed. The GC % of a nucleotide sequence may differ from the GC % of the host cell.

In embodiments, the GC % of the targeted nucleotide sequence may be within at least 15, 10, or 5 percentage points of the GC % of the host cell. By way of example, if a host cell has a GC % equal to 51%, then the GC % of the targeted nucleic acid sequence may be from 46% to 56% when a 5 percentage point allowance is used. Preferably, the use of a nucleotide sequence that corresponds to the GC % of the host cell contributes to the upregulation of spider silk protein. In some embodiments, expression systems that employ sequences modified as described above may also provide tRNAs having anticodons that recognize the codons provided by the modified nucleic acid sequence, as described above.

V. Applications

Synthetic spider silk proteins produced by the methods described herein may be spun into a fiber, or otherwise incorporated or formed into a fiber, by any means known in the art, whether the means are presently known or developed in the future. Spider sink proteins may also be used to make powders or thin films for use in coatings of medical devices or for other uses. By way of example, synthetic spider silk proteins produced by the methods described herein may be useful in artificial tendons and ligaments, bullet proof vests, airbags, athletic gear, parachutes, aircraft landing cables, biomedical sutures, drug delivery systems, cables, and other products where the properties of synthetic spider silk or spider silk fibers may be desired.

EXAMPLES

The following examples are illustrative only and are not intended to limit the disclosure in any way.

In Examples 1-6, recombinant spider silk sequences were modified so that codon usage corresponds to the tRNA pool available in *E. coli*. The result is that *E. coli* is a more effective expression system for the production of highly repetitive recombinant spider silk proteins (rSSP). Six of these optimized rSSg's have been produced to be placed into the enhanced rSSP expression vector (Examples 1-6). In Example 7, an additional, unmodified, rSSg has also been inserted into pET-SX to demonstrate the efficiency of increasing the tRNA pools of glycine, alanine and proline as well as the conversion of existing serine to glycine via the SHMT of the new vector in comparison to a traditional expression vector (pET-19k). Referring now to FIG. 13, there is shown the expression of MaSP1 from pET-19 and pET-SX.

Example 1

Preparation of MaSP1 Expression Vector

An expression vector having a DNA sequence (SEQ ID NO:1) encoding the recombinant spider silk amino acid sequence (SEQ ID NO:2) was developed. After its design, the DNA sequence was produced by Life Technologies in the pMK-RQ vector. To increase the size of this insert, it was doubled utilizing compatible but nonregenerable restriction sites. In this case, the restriction sites used were 5'-AgeI and 3'-BsPEI in combination with a unique restriction site (NcoI) on the pMK-RQ vector. The NcoI-AgeI and NcoI-BspEI fragments, each containing one copy of the cloned monomer sequence, were ligated together, thus effectively regenerating a full plasmid while doubling the size of the monomer insert in the process.

Referring now to FIG. 1, shown are the restriction enzymes and their restriction sites, including HindIII (underlined AAGCTT), NdeI (underlined CATATG), AgeI (underlined ACCGGT), BspEI (underlined TCCGGA) and BamHI (underlined GGATCC), for the DNA sequence SEQ ID NO:1 that encodes the MaSP1 amino acid sequence shown in FIG. 2 and SEQ ID NO:2.

The regenerated plasmid containing the doubled silk insert was cloned into bacteria and used as a template in the next cloning step. After multiple rounds of cloning, this strategy increased the size of the silk-like insert to the desired number of motif repeats. For MaSP1, the motif was repeated 2, 3, 4, and 8 times. Once the desired size of insert was achieved through the outlined steps above, the synthetic spider silk gene as released from the recombinant pMK-RQ vector by restriction digestion in 5' with NdeI and in 3' by BamHI.

The purified insert was cloned in frame into the expression vector (pET-19b and pET-SX) at the NdeI/BamHI sites for expression of the protein.

Example 2

Preparation of MaSP2 Expression Vector

An expression vector having a DNA sequence (SEQ ID NO:3) encoding a recombinant spider silk amino acid sequence (SEQ ID NO:4) was developed according to the steps outlined in Example 1.

Referring now to FIG. 3, shown are the restriction enzymes and their restriction sites, including HindIII (underlined AAGCTT), NdeI (underlined CATATG), AgeI (underlined ACCGGT), BspEI (underlined TCCGGA) and BamHI (underlined GGATCC), for the DNA sequence SEQ ID NO:3 that encodes the MaSP1 amino acid sequence shown in FIG. 4 and SEQ ID NO:4.

Example 3

Preparation of MiSP Expression Vector

An expression vector having a DNA sequence (SEQ ID NO:5) encoding a recombinant spider silk amino acid sequence (SEQ ID NO:6) was developed according to the steps outlined in Example 1. For MiSP, the motif was repeated 2, 3, 4, and 8 times.

Referring now to FIG. 5, shown are the restriction enzymes and their restriction sites, including HindIII (underlined AAGCTT), NdeI (underlined CATATG), AgeI (underlined ACCGGT), BspEI (underlined TCCGGA) and BamHI (underlined GGATCC), for the DNA sequence SEQ ID NO:5 that encodes the MiSP amino acid sequence shown in FIG. 6 and SEQ ID NO:6.

Example 4

Preparation of FLYS Expression Vector

An expression vector having a DNA sequence (SEQ ID NO:7) encoding the recombinant spider silk amino acid sequence (SEQ ID NO:8) was developed. After its design, the DNA sequence was produced by Life Technologies in the pMA-RQ vector. To increase the size of this insert, it is doubled utilizing compatible but nonregenerable restriction sites. In this case, the restriction sites used were 5'-XmaI and 3'-BsPEI in combination with a unique restriction site (PvuI) on the pMA-RQ vector.

The PvuI-XmaI and PvuI-BspEI fragments, each containing one copy of the cloned monomer sequence, were ligated together, thus, effectively regenerating a full plasmid while doubling the size of the monomer insert in the process.

The regenerated plasmid containing the doubled silk insert was cloned into bacteria and used as a template in the next cloning step. After many rounds of cloning, this strategy increased the size of the silk-like insert to the desired number of motif repeats. For FLYS, the motif was repeated 2, 3, 4, and 8 times. Once the desired size of insert was achieved through the outlined steps above, the synthetic spider silk gene is released from the recombinant pMA-RQ vector by restriction digestion in 5' with NdeI and in 3' by BamHI.

The purified insert as cloned in frame into the expression vector (pET-19b and pET-SX) at the NdeI/BamHI sites for expression of the protein.

Referring now to FIG. 7, shown are the restriction enzymes and their restriction sites, including HindIII (underlined AAGCTT), NdeI (underlined CATATG), XmaI (IS THIS CORRECT) (underlined CCCGGG), BspEI (underlined TCCGGA) and BamHI (underlined GGATCC), for the DNA sequence SEQ ID NO:7 that encodes the FLYS amino acid sequence shown in FIG. 8 and SEQ ID NO:8.

Example 5

Preparation of ACSP Expression Vector

An expression vector having a DNA sequence (SEQ ID NO:9) encoding the recombinant spider silk amino acid sequence (SEQ ID NO:10) was developed. The size of the module was doubled by manipulating separately the recombinant vector with each one of the flanking compatible but nonregenerable restriction sites (5-AgeI and 3'-BspEI), in combination with a unique restriction site (PvuI) on the pMA-T vector the insert was supplied in from Life Technologies.

The PvuI-AgeI and PvuI-BspEI fragments, each containing one copy of the cloned monomer sequence, were ligated together, thus, effectively regenerating a full plasmid while doubling the size of the monomer insert in the process. The regenerated plasmid containing the doubled silk insert was transformed into bacteria and used as a template in the next cloning step.

After the desired number of rounds of cloning (doubling the insert size), this strategy increased the size of the silk-like insert to a defined number of motif repeats. For AcSp, the motif was repeated 4, 6, and 8 times its original length.

The synthetic spider silk gene was released from the recombinant pMA-T vector by restriction digestion in 5' with NdeI and in 3' by BamHI The purified insert was cloned in frame into the expression vector (pET-19b and pET-SX) at the NdeI/BamHI sites for expression of the protein.

Referring now to FIG. 9, shown are the restriction enzymes and their restriction sites, including HindIII (underlined AAGCTT), NdeI (underlined CATATG), AgeI (underlined CCCGGG), BspEI (underlined TCCGGA) and BamHI (underlined GGATCC), for the DNA sequence SEQ ID NO:9 that encodes the ACSP amino acid sequence shown in FIG. 10 and SEQ ID NO:10.

Example 6

Preparation of MaSP2 Expression Vector and Protein Expression

An expression vector having a DNA sequence (SEQ ID NO:11 and FIG. 11) encoding the recombinant spider silk amino acid sequence (SEQ ID NO:12 and FIG. 12) was developed. The DNA segment, with an Xma I cut on the 5' end (with respect to the coding strand) and the other end blunt but containing a Bsp EI site, was ligated into pBluescript II (Stratagene) which had been double digested with Xma I and Eco RV and agarose gel purified, thus giving a directional cloning with the inserted segment in frame with the lac I gene of pBluescript II. It is important to note for the strategy explained later that Xma I and Bsp E I have compatible, nonregenerable overlaps (DNA cut with these enzymes can be ligated, but will not regenerate either site). The ligated DNA was subjected to Eco RI digestion to reduce background (the Xma I, Eco RV digest of the vector eliminated the unique Eco RI site of pBluescript II) and used to transform Sure competent cells (Stratagene). Twelve white colonies resulted which were screened by miniprepping the plasmid (MaxiScreen, J. T. Baker), and digesting the DNA with BssHII to release the insert. An agarose gel was used to determine if the white colonies contained plasmids with an appropriate size. Four colonies contained inserts of the predicted size, and DNA was prepared by MaxiScreen and subjected to sequencing.

Fermentation Method:
A seed culture of MaSp2 in both pET-SX and pET19K was prepared by picking a single colony from a plate and inoculating 60 ml's of fresh LB media with kanamycin for selectivity. The seed culture was allowed to grow to an OD$_{600}$ of 4-6. At that point the cells were harvested by centrifugation and resuspended in 60 ml's of fresh media. The seed culture is then used to inoculate a 5 L fermentation.

The MaSP2 clone was grown at 37 C in BioFLo fermenter. The components in Table 1 were autoclaved along with the necessary feed lines (for glycerol and antifoam). Once the ideal temperature (37 C) was reached, the components in Table 2 were added. A cascade program was written to maintain pH at 7.0 (by addition of NaOH) and dissolved $O_2$ was maintained at approximately 40%. The seed culture was then inoculated into the 5 L BioFlo fermentor and OD measured at several time points. A continuous supply of glycerol (source of C) started after 5 h of inoculation. When A600 reached 15-18, production of silk was induced by adding 0.5 mM IPTG, along with 50% ammonium sulfate and glycerol added initially, as C and N source. After 4 h induction, the cells were harvested by centrifugation and frozen at −80 C until use.

TABLE 1

Autoclave components

| Component | g/L |
|---|---|
| $KH_2PO_4$ | 2.0 |
| $K_2HPO_4$ | 3.0 |
| $(NH_4)_2HPO_4$ | 5.0 |
| Yeast extract | 5.0 |

TABLE 2

Additional autoclave components

| Component | /L |
|---|---|
| Kanamycin | 50 mg |
| Glycerol | 9.5 g |
| Sterile trace metals | 5 mL |
| Sterile thiamine | 0.05 mL |
| Sterile $MgSO_4 \cdot 7H_2O$ | 2.5 mL |
| Autoclaved 50% glucose | 6.5 ml |
| K12 trace metal | g/L |
| NaCl | 5.0 |
| $ZnSO_4 \cdot 7H_2O$ | 1.0 |
| $MnCl_2 \cdot 4H_2O$ | 4.0 |
| $FeCl_3 \cdot 6H_2O$ | 4.75 |
| $CuSO_4 \cdot 5H_2O$ | 0.4 |
| $H_3BO_3$ (Boric Acid) | 0.575 |
| $Na_2MoO_4 \cdot 2H_2O$ | 0.5 |
| 6N $H_2SO_4$ | 12.5 mL/L** |

**Can vary between 8-20 mL, whatever is needed to dissolve the other component

Expression Comparison of MaSP2 in pET-19k and pET-SX.

Two fermentations were run under identical conditions as described above. After completion of the fermentation a western blot was run on both the pET-19k expressing MaSP2 and pET-SX expressing the same to identify if the addition of the glycine, alanine and proline tRNA's as well as the SHMT sequence improved the expression of rSSP.

Figure 14:
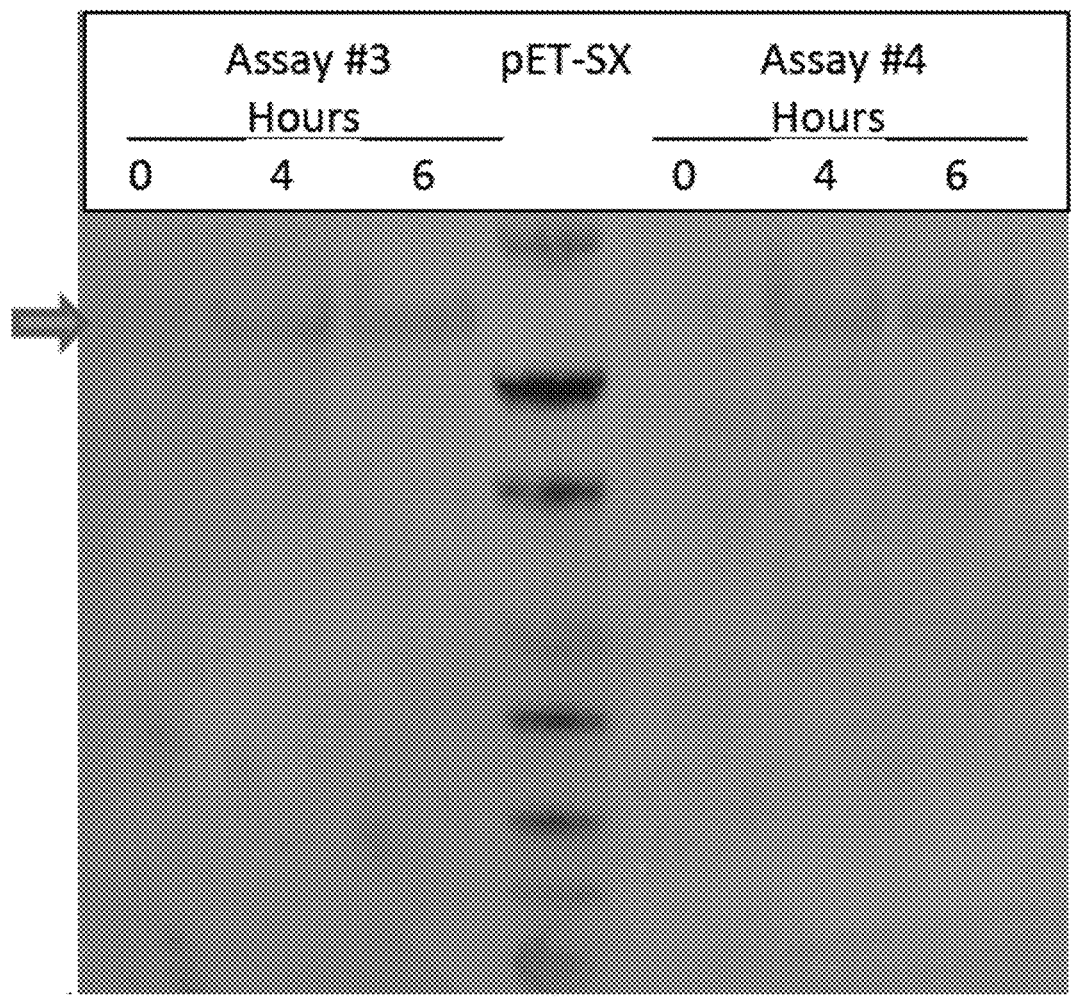
FIG. 14 depicts MaSP2 protein expression using the pET-19K as the expression vector.
Figure 15:
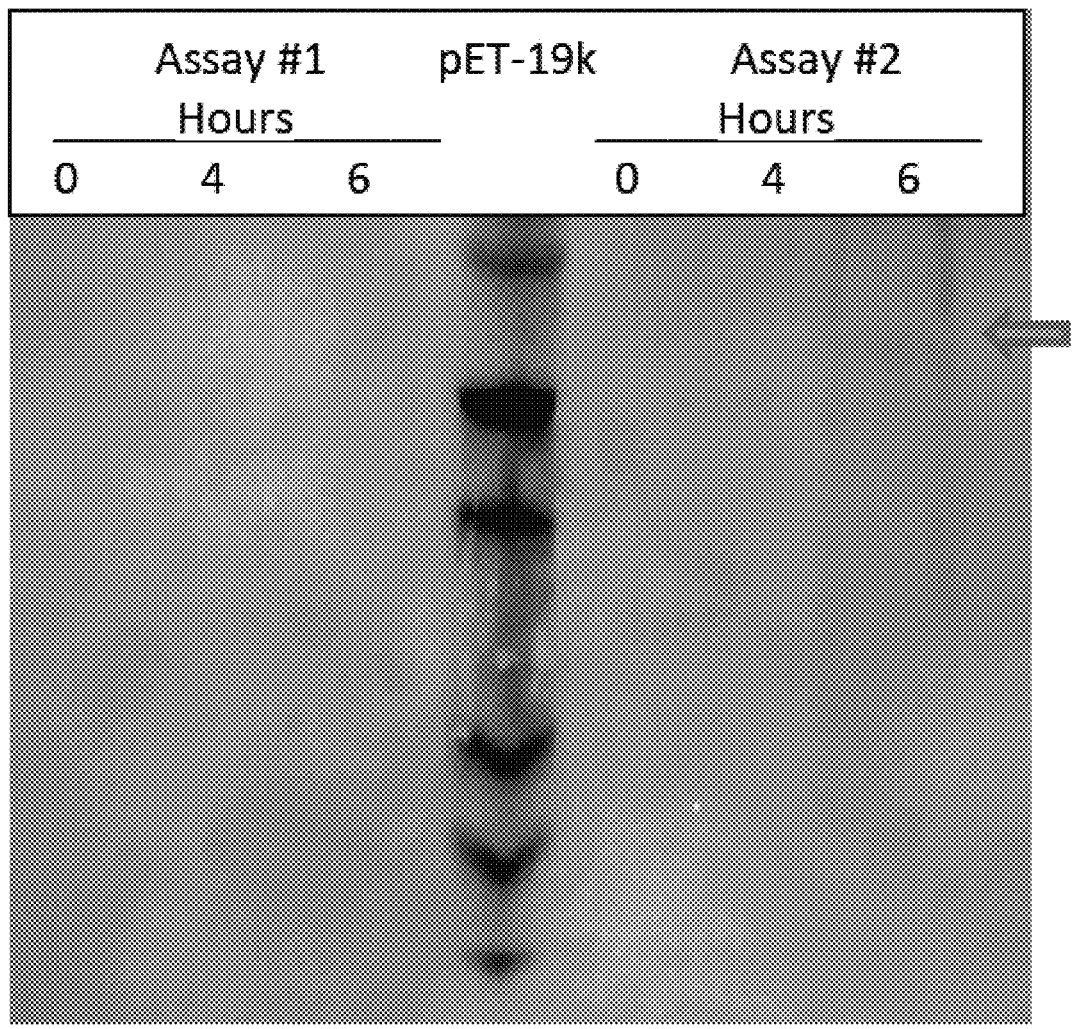
FIG. 15 depicts MaSP2 protein expression using the pET-SX vector.

As shown in FIG. 14, assays 3 and 4, which were done using pET-SX as the expression vector, clearly show an accumulation of the MaSP2 protein. Assays 1 and 2, as shown in FIG. 15, using the traditional pET-19K as the expression vector, only show a slight accumulation of the MaSP2 protein when compared to assays 3 and 4 in the pET-SX vector.

Example 7

Providing Increased Glycine and Select tRNAs

Referring now to FIG. 16, there is shown sequence SEQ ID NO:23 from a pET19-SX (Kan) expression vector for upregulating the production of synthetic spider silk polypeptides. The pET19-SX (Kan) was designed to compensate for insufficient t-RNAs for glycine and proline and a lack of sufficient glycine. The GlyT, ProL and ProM t-RNAs were included a pET19 (Kan) vector. Additionally serine hydroxymethyl transferase was included as part of the vector to transform serine to glycine. All of these four genes were derived from *E. coli* via PCR for incorporation into the vector.

Figure 17:
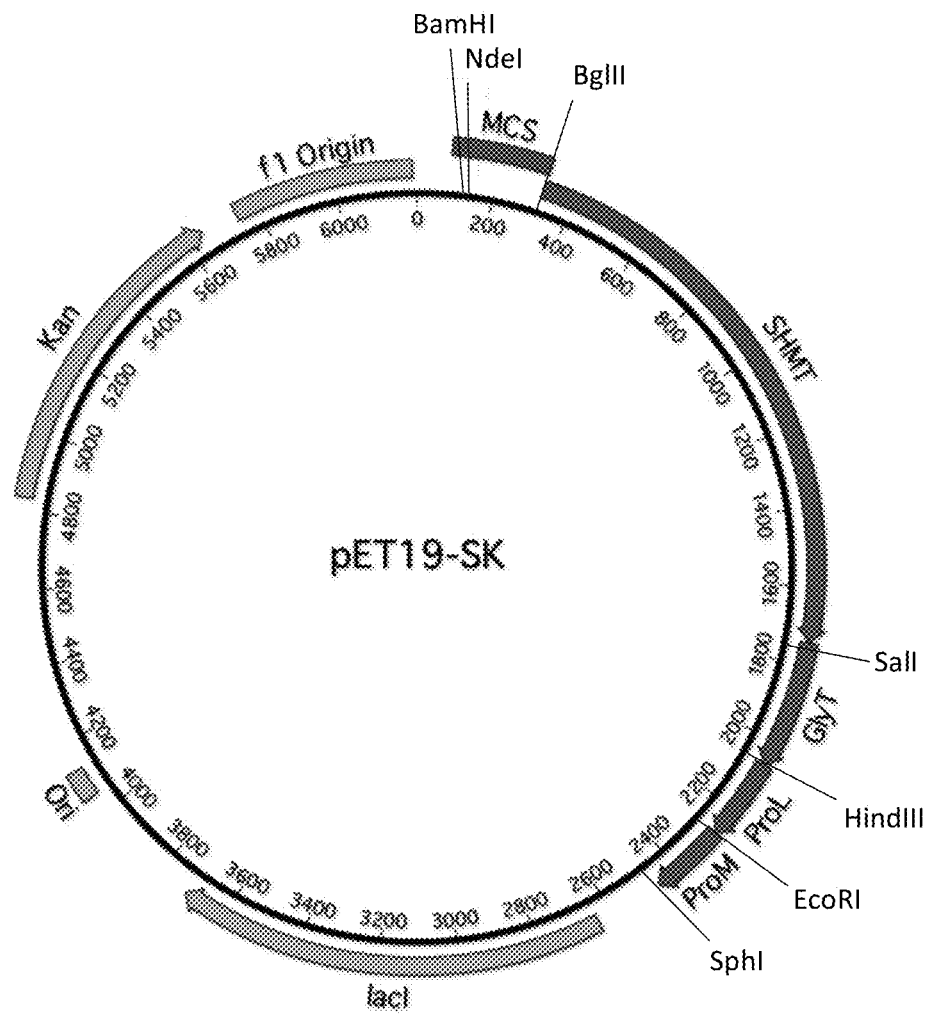
FIG. 17 depicts pET19-SX, an exemplary expression vector designed for expression of spider silk proteins in *Escherichia coli*.

In further detail, and referring now to FIG. 17, pET19-SX is an altered pET19-b expression vector designed for optimized expression of spider silk proteins in *Escherichia coli*. To increase spider silk protein yield additional proline and glycine (the two most prominent amino acids in spider silk) tRNAs were added to drive translation. pET19-SX has the sequence for one glycine tRNA (GlyT), two proline tRNAs (ProL and ProM), and a serine hydroxymethyltransferase (SHMT), an enzyme that catalyzes the conversion of serine into glycine. With the addition of these four sequences the expression vector may have been too large to optimally express the large (≥200 kDa) spider silk protein. To address this possible issue 1,530 base pairs, that are believed to not affect translation or expression, were removed between the Ori and lacI site. Expression vectors such as the one shown in Figure CC may be combined with other expression vectors that encode synthetic spider silk polypeptides, to provide an expression system for the upregulation of production of spider silk proteins.

Figure 18:
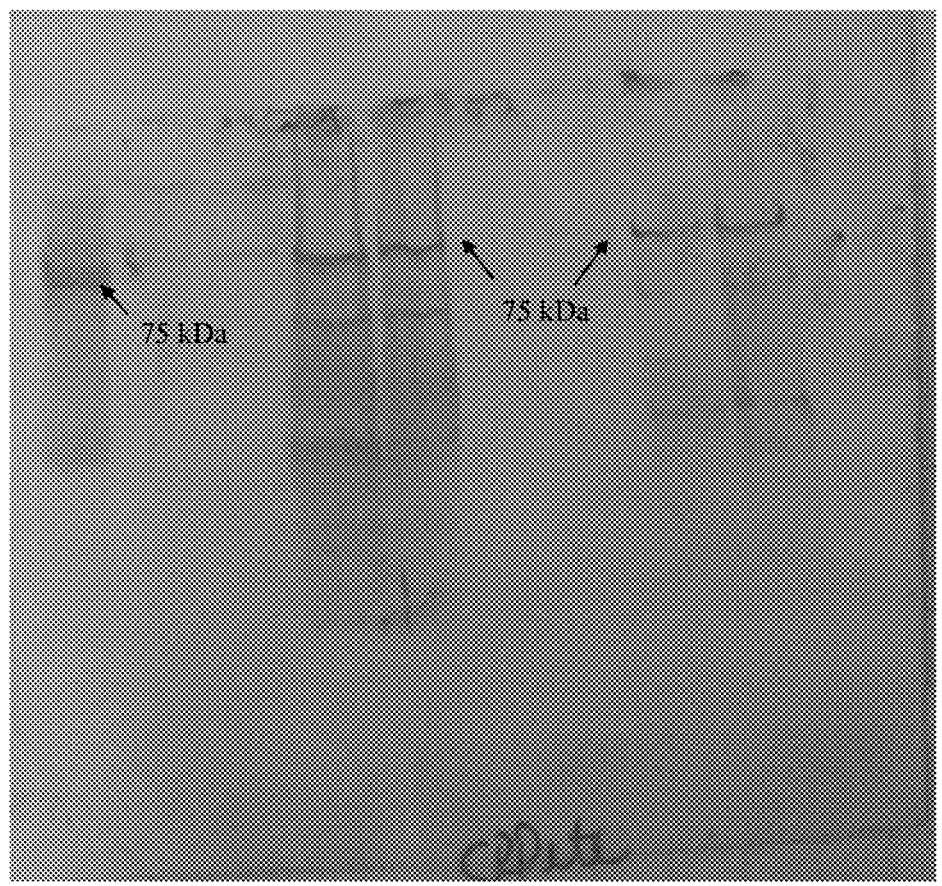
FIG. 18 depicts a protein band at 75 kDa, expected from a 2190 bp Pix3 DNA construct.

Referring now to FIG. 18, *E. Coli* containing pET-SX (6974 bp) was grown in LB media containing 0.5 g of Kanamycin. The pET_SX plasmid was extracted using Qiagen Mini-prep kit (Cat. No. 27104). The plasmid was digested using BamHI and NdeI restriction enzymes. The plasmid was run on a 1% agarose gel. The band containing linearized pET_SX plasmid was excised, and the DNA extracted using a Qiagen Gel Extraction kit (Cat. No. 28704). The insert was also digested with BamHI and NdeI at 37 C for 1 hour, and purified using gel electrophoresis and a Qiagen Gel Extraction kit in the same manner as the plasmid. The insert (Pix3, 2190 bp) was ligated into the pET_SX plasmid using T4 ligase. A 4:1 ratio of insert to vector by mass was used to create a 20 microliter reaction. This reaction was left overnight at 14 C, and the DNA was concentrated by ethanol precipitation.

The concentrated DNA was mixed with electrocompetent BL21DE3 *e. Coli* cells and left to rest on ice for 15 minutes. The cells were then electroporated at 1800V. The cells resuspended in 1 ml of LB and left to grow at 37 C and 245 RPM for 60 minutes. Cells were then concentrated by centrifugation (15000 RCF, 5 seconds), and resuspended in 200 microliters of LB. This was spread on a Kanamycin (50 micrograms/ml) LB plate and grown at 37 C overnight. Colonies were selected, and used to inoculate 6 ml aliquots of LB(kan) media. These aliquots were grown overnight. From each culture, 1 ml was concentrated in a 1.7 ml tube by centrifugation (15000 RCF for 1 minute). The supernatant was discarded, and the cell pellet was resuspended in sterile 10% glycerol. These stocks were stored at −80 C. The plasmid DNA contained in the remaining 5 ml cultures was extracted using a Qiagen Mini-prep kit. Each of these were digested with BamHI and NdeI restriction enzymes for 1 hour at 37 C. Gel electrophoresis for each digested colony prep was done, and a single colony containing bands of appropriate size were selected (2190 bp and 6974 bp). The glycerol stock corresponding to this colony was streaked onto an LB(kan) plate, and grown overnight at 37 C. A single colony from this plate, selected at random, was used to inoculate a 50 ml culture of LB(kan) media. This was grown overnight at 37 C and 245 RPMs.

The culture was concentrated by centrifugation (2012RCF for 10 minutes), and resuspended in 50 ml of fresh LB(kan) media. A 1 liter-volume of LB(kan) in a baffled culture flask was inoculated with the 50 ml culture. This was grown at 37 C and 245 RPMs to an optical density of 0.8 at 600 nm. The culture was then induced with 0.24 g of IPTG, and grown for 4 hours at 37 C and 245 RPMs. Cells from the culture were concentrated by centrifugation (2012 RCF, 20 minutes), and the supernatant discarded. The cells were resuspended in NPI-5 buffer at a 3×ml buffer volume/mg wet cells ratio (300 ml NPI-5 buffer to resuspend 100 mg wet cell paste). This was stored at −20 C until frozen. The sample was thawed and sonicated (27 W for 1 minute). 20 microliters of the sample was mixed with 20 microliters of 2×SABU loading buffer, and boiled for 10 minutes. The sample was then loaded onto a 4-20% SDS-PAGE, and run at 100 mV for 72 minutes. A transfer to a nitrocellulose membrane was done for 70 minutes at 100 mA in Towbin transfer buffer. The membrane was blocked for 1 hour in 30 ml of blocking solution (5 g of Carnation milk in 100 ml of TBST buffer). Two washes (10 minutes each) in 30 ml of TBST buffer were done to remove blocking solution. 3 microliters of primary anti-6×Histidine antibody were added to 30 ml of blocking solution (1:10, 000), and applied to the membrane for 1 hour. This was followed by two 10 minute washes in TBST buffer. 3 microliters of secondary alkaline phosphatase antibody was added to 30 ml of blocking solution (1:10,000), and applied to the membrane for 1 hour. This was followed by two 10 minute washes in TBST buffer. OneStep BST/NCIP AP development buffer was then applied to the membrane until sufficient color development occurred. The membrane was then washed with distilled water to stop development.

Acronyms (as used in this example):
LB—Luria Broth
Kan—Kanamycin
IPTG—Isopropyl Thiogalactoside
TBST—Tris buffered saline with 0.05% Tween-20
SaBU—Sample buffer with urea
AP—Alkaline Phosphatate
SDS-PAGE—Sodium dodecyl sulfide polyacrylamide gel electrophoresis
RPM—revolutions per minute
RCF— relative centrifugal force
E. Coli strain BL21DE3 was used as follows:
Buffer Recipes:
50×TAE Buffer: 242 g Tris, 57.1 HOAc, 100 ml 0.5M EDTA in 1 L of ddH20.
10× Running Buffer: 10 g SDS, 121 g Tris, 238 g HEPES in 1 L ddH20.
2× Towbin Buffer: 40 ml of 1M Tris, 57.65 g Glycine, 400 ml Methanol in 2 L ddH20.
TBST Buffer: 7.2 g Tris, 24 g NaCl, 1.5 ml Tween20 in 3 L of ddH20. pH to 7.4 with HCl
NPI-5 Buffer: 34.39 g NaH2PO4, 87.66 g NaCl, 1.702 g Imidizole, 2042.2 g Urea in 5 L ddH20.
SaBU: 8M Urea, 6M EDTA, 10% SDS, 10% glycerol, 0.4% bromphenol, 125 micromolar Tris-HCl, 5% betamercaptoeathanol, pH to 6.7.

Example 8

Upregulation of Spider Silk Production in E. coli with the Use of Specific tRNAs Spiders can produce six different fibers one of which is the major ampullate dragline silk. Dragline silk consists of two proteins: the major ampullate spidroin 1& 2 (MaSP1 & MaSP2) and can be produced in different species of spiders such as Nepila clavipes and Argiope aurantia.

The MaSP2 protein make-up can consist of different levels of elastic unit. These are denoted as 1E and 2E, where 1 is a single elastic unit and 2 is a double elastic unit. The spider silk subunit chosen for optimized production in E. coli was the amino acid sequence SEQ ID NO:13 for MaSP2 Argiope aurantia and contains 2 repeats of the elastic unit: (GGYG-PGAGQQGPGSQGPGSGGQQGPGGQ, SEQ ID NO: 26) followed by 6 polyalanines, which is based on Brooks et al., Properties of synthetic spider silk fibers based on Argiope aurantia MaSp2. Biomacromolecules 9:1506-1510 (2008).

Design and Optimization of Spider Silk Sequences for tRNA Usage:

Due in part to the use of only six amino acids in spider silk proteins, overexpression of the silk protein can lead to the depletion of charged tRNA molecules in a host cell, which can either prevent the host cell from making spider silk proteins or result in reduced yield of the proteins. Codon optimization for specific tRNAs was performed 'by hand' based on the amino acid sequence. The list of tRNA genes in E. coli K-12 (related to the lab strains of E. coli: XL1 Blue and BL21) was acquired from the Genomic tRNA Database (accessed September 2012). Specific codons were chosen so that they contained the lowest possible GC % for that specific amino acid. The spider silk 2E construct that was designed using the fewest tRNA codons is denoted 'F' and only uses one codon for each amino acid. The balanced tRNA codon construct, or 'B' construct, uses two codons for glycine (ggt, gaa), proline (cct, cca), and serine (agt, tct) as these were the only amino acids out of the six that had multiple codons options with low GC %. Alanine also possessed two codons with low GC % that had known E. coli tRNAs, but additional codons could not be utilized as it would have created PstI restriction sites in the silk construct.

TABLE 3

Codon usage for one repeat of an exemplary spider silk amino acid sequence.

| | | | % Codon Usage | | |
|---|---|---|---|---|---|
| Amino Acid | % Composition | Codon | Unoptimized (W) | Fewest (F) | Balanced (B) |
| Ala (A): | 11.80 | GCT | 25 | 0 | 0 |
| | | GCC | 25 | 0 | 0 |
| | | GCA | 25 | 100 | 100 |
| | | GCG | 25 | 0 | 0 |
| Gln (Q): | 17.6 | CAA | 33 | 100 | 100 |
| | | CAG | 67 | 0 | 0 |
| Gly (G): | 44.1 | GGT | 57 | 100 | 50 |
| | | GGC | 40 | 0 | 0 |
| | | GGA | 0 | 0 | 50 |
| | | GGG | 3 | 0 | 0 |
| Pro (P): | 14.7 | CCT | 0 | 100 | 50 |
| | | CCC | 0 | 0 | 0 |
| | | CCA | 0 | 0 | 50 |
| | | CCG | 100 | 0 | 0 |

TABLE 3-continued

Codon usage for one repeat of an exemplary spider silk amino acid sequence.

| Amino Acid | % Composition | Codon | % Codon Usage | | |
|---|---|---|---|---|---|
| | | | Unoptimized (W) | Fewest (F) | Balanced (B) |
| Ser (S): | 7.4 | TCT | 0 | 0 | 40 |
| | | TCC | 0 | 0 | 0 |
| | | TCA | 0 | 0 | 0 |
| | | TCG | 0 | 0 | 0 |
| | | AGT | 0 | 100 | 60 |
| | | AGC | 100 | 0 | 0 |
| Tyr (Y): | 4.4 | TAT | 100 | 100 | 100 |
| | | TAC | 0 | 0 | 0 |

Having PstI sites conflicts with the cloning procedure used, so only a single codon for Alanine was used in the 'B' construct. Distribution of the different codons in the B' construct was also taken under consideration where, the two codons for the glycine, proline, and serine amino acids were distributed evenly. Table 3 demonstrates the codon usage for each of the different sequences.

Referring again to Table 3, MaSp2 *A. aurantia* spider silk proteins were encoded using DNA sequences with variations in codon usage. Unoptimized DNA sequence (W), Fewest (F), and Balanced (B) codon variations were generated. As shown in the table, the approach for constructing a DNA using the fewest number of codons possible results in having one codon for each corresponding amino acid. Not shown are the codons for the scar region (2 amino acids that are between each of the spider silk subunits): T-Threonine (ACT codon) and R-Arginine (AGA codon).

Table 4 demonstrates the complete sequences for the 'W', 'F', and 'B' constructs. Additional spider silk DNA pieces were also created to contain a start codon (atg) to allow for direct translation of the DNA sequence. These start codon were added to each 'W', 'F', and 'B' spider silk piece with the use of mutagenesis primers and a site directed mutagenesis kit (Agilent Technologies, Santa Clara, Calif.). These new pieces are termed 'atgW', 'atgF', and 'atgB.' Complete sequences are provided in Table 4. All cloning and expression was carried out in pSB1C3 plasmid.

tRNA Construction:

FIG. 20, corresponding to SEQ ID NO:21, shows DNA construct that provides a recombinant nucleotide sequence encoding six tRNAs for increased spider silk expression. Shown is an 812 base pair sequence that may be generated through traditional molecular biology techniques, including PCR and restriction digestion, or may be chemically synthesized. All of the promoters for the tRNA genes used in the tRNA overexpression constructs are exactly the same. The sequence used is based on the ZH14 sequence from the study by Bauer et al. (1993). This promoter was selected from a list of tRNA promoters and is based on mutations made to the leuV tRNA promoter from *E. coli*, and has approximately normal growth-rate dependent regulation but 12 times normal promoter strength. FIG. 21, corresponding to SEQ ID NO:22 shows additional tRNA constructs used in this study.

TABLE 4

Amino acid sequence, unoptimized DNA sequence, fewest codon usage DNA sequence, and balance codon usage DNA sequence for MaSp2 *A. aurantia* spider silk.

| | | |
|---|---|---|
| Amino acid sequence for MaSp2 A. aurantia spider silk | SEQ ID NO: 13 | GGYGPGAGQQGPGSQGPGSGGQQGPGGQGGYGPGAGQQ GPGSQGPGSGGQQGPGGQAAAAAA |
| Amino acid sequence for MaSp2 A. aurantia spider silk containing a start (methionine) | SEQ ID NO: 14 | <u>M</u>GGYGPGAGQQGPGSQGPGSGGQQGPGGQGGYGPGAGQ QGPGSQGPGSGGQQGPGGQAAAAAA |
| Unoptimized DNA sequence ('W') | SEQ ID NO: 15 | ggcggttatggtccgggcgccggccagcaaggtccgggcagccaggtccgggcagcg gtggccaacagggtccgggtggtcagggcggttatggtccgggcgccggccagcaaggtc cgggcagccaggtccgggcagcggtggccaacagggtccgggtggtcaggggccgtat ggtccgagcgctgcggcagcggctgca |
| Fewest codon DNA sequence ('F') | SEQ ID NO: 16 | ggtggttatggtcctggtgcaggtcaacaaggtcctggtagtcaaggtcctggtagtggtggt caacaaggtcctggtggtcaaggtggttatggtcctggtgcaggtcaacaaggtcctggtagt caaggtcctggtagtggtggtcaacaaggtcctggtggtcaaggtccttatggtcctagtgca gcagcagcagca |
| Balanced codon DNA sequence ('B') | SEQ ID NO: 17 | ggtggatatggtcctggagcaggtcaacaaggaccaggtagtcaaggacctggttctggag gtcaacaaggaccaggtggacaaggtggatatggtcctggagcaggtcaacaaggaccag gtagtcaaggacctggttctggaggtcaacaaggaccaggtggacaaggtccttatggacca agtgcagcagcagcagcagca |
| Unoptimized DNA sequence ('atgW') with atg (start codon) | SEQ ID NO: 18 | <u>atg</u>ggcggttatggtccgggcgccggccagcaaggtccgggcagccaggtccgggcag cggtggccaacagggtccgggtggtcagggcggttatggtccgggcgccggccagcaag gtccgggcagccaggtccgggcagcggtggccaacagggtccgggtggtcagggcc gtatggtccgagcgctgcggcagcggctgca |
| Fewest codon DNA sequence ('atgF') | SEQ ID NO: 19 | <u>atg</u>ggtggttatggtcctggtgcaggtcaacaaggtcctggtagtcaaggtcctggtagtggt ggtcaacaaggtcctggtggtcaaggtggttatggtcctggtgcaggtcaacaaggtcctggt agtcaaggtcctggtagtggtggtcaacaaggtcctggtggtcaaggtccttatggtcctagtg cagcagcagcagcagca |

TABLE 4-continued

Amino acid sequence, unoptimized DNA sequence, fewest codon usage DNA sequence, and balance codon usage DNA sequence for MaSp2 A. aurantia spider silk.

| Balanced codon DNA sequence ('atgB') | SEQ ID NO: 20 | atgggtggatatggtcctggagcaggtcaacaaggaccaggtagtcaaggacctggttctg gaggtcaacaaggaccaggtggacaaggtggatatggtcctggagcaggtcaacaaggac caggtagtcaaggacctggttctggaggtcaacaaggaccaggtggacaaggtccttatgga ccaagtgcagcagcagcagcagca |
|---|---|---|

Referring now to FIG. 19, the nucleotide and amino acid sequence for balanced SEQ ID NO:17 sequence 'B' from Table 4 is shown with the amino acids over the condons. Codon usage was as follows: glycine (G=2 (ggt, gaa)), tyrosine (Y=1 (tat)), proline (P=2(cct, cca)), alanine (A=1 (gca)), glutamine (Q=1 (caa)), and serine (S=2 (agt, tct)). The GC content of the DNA sequence is approximately 55%.

Another consideration was the choice of the tRNA terminator. The same identical terminator was used for each tRNA gene. This terminator is based on the downstream sequence of the E. coli Ala (GCC) tRNA. It contains the region of 3-6 T's that is common characteristic of tRNA terminators and an additional 10 bp of native sequence that ensures RNA termination and also a spacer between to the next gene.

The tRNA sequences for use in overexpression were selected from the Genomic tRNA Database for E. coli K-12, a strain of E. coli closely related to the strains used in this study, XL1 Blue and BL21, and whose genome is the most extensively annotated. tRNA sequences with anti-codons recognizing the codons used in the 'B' and 'F' subunits were selected, and their native sequences used. Two sets of tRNA genes were selected for overexpression constructs. The six tRNAs (FIG. 20) corresponding to the codons used in the 'F' construct were made into a single construct with each gene preceded by a tRNA promoter and followed by a terminator sequence. The additional tRNAs for the glycine, proline, and serine amino acids were included in the second construct (FIG. 21), as well as two additional tRNAs that had anticodons matching the threonine and arginine amino acids that would be generated in the scar sites from use of the BioBrick Assembly Standard #23 cloning method. Both tRNA constructs have been co-expressed on a single plasmid pSB3K3 which has compatible antibiotics and origins of replication to pSB1C3.

Construction of Complete Spider Silk Expression System:

All spider silk constructs were assembled in pSB1C3 (PartsRegistry.org) according to BioBrick standards (Knight 2003; Phillips and Silver 2006). All the spider silk repeat units as well as the 10×His-tag were assembled according to RFC 23, which allows for protein fusions. Transformations were carried out via electroporation or chemical/heat shock into E. coli XL1-Blue and BL21 (Agilent Technologies, Santa Clara, Calif.). All spider silk cloning was carried out in XL1 blue and expression studies were carried out in BL21.

The Lac promoter and ribosome binding site (BBa_K208010) was used as it had been previously demonstrated to work in other protein expression systems such as that for GFP expression and translocation (Linton, Walsh et al. 2011) and phasin/polyhydroxybutyrate secretion (Rahman, Linton et al. 2013).

Figure 22:
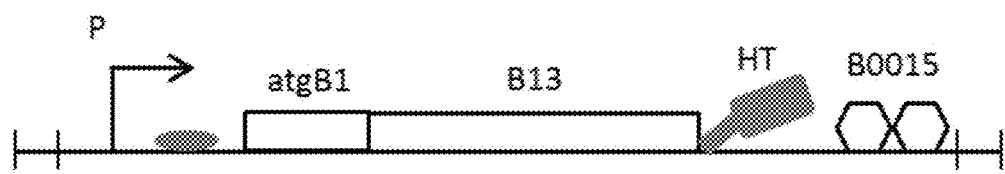
FIG. 22 depicts a representation of the spider silk production system in pSB1C3.

One MaSp2 spider silk subunit gene, (containing a start codon atg, e.g. 'atgF' or 'atgB' Table 4), was first cloned proceeding the promoter and ribosome binding site by cutting the pSB1C3 vector (contain the promoter and ribosome binding site) with SpeI and PstI restriction enzymes. The first spider silk repeat (also in pSB1C3) was digested with XbaI and PstI (called the 'insert'). The resulting 'vector' was ligated with 'insert' to create a new plasmid with promoter, ribosome binding site, and 1 repeat of spider silk DNA (containing the atg). Subsequent cloning of additional 13 spider silk repeats of 'B' (Table 4, SEQ ID NO:17) resulted in a larger repetitive spider silk sequence. Finally the 10×His-tag (BBa_K844000, PartsRegistry.org) and double terminator (BBa_B0015, PartsRegistry.org) were subsequently cloned into the system to give a full construct patgB14HT (where 'p' is the promoter and ribosome bind site, atg is the start codon, B14 is fourteen repeats of 'B' spider silk, and HT is the 10×His-tag). The 10×His-tag was placed at the C-terminal end to ensure that only fully translated spider silk protein was purified. Sequencing was carried out using VF2 (tgccacctgacgtctaagaa, SEQ ID NO:24) and VR (attaccgcctttgagtgagc, SEQ ID NO:25) primers to confirm correct DNA construction. FIG. 22 shows a representation of the spider silk production system in pSB1C3.

Construction of a Spider-Silk GFP Fusion:

Spider silk expression systems comprising a DNA construct that incorporates the green fluorescent protein (GFP) after the spider silk gene repeats has been constructed. The expression of GFP allows for indirect monitoring of spider silk production by visualization of GFP. Since the GFP is only expressed if the full length spider silk proteins are being produced, GFP expression indicates expression of the full spider silk construct. The DNA construct comprises, in order, a promoter, silk gene repeats, GFP, His-tag and a terminator. By way of example, a DNA construct comprising, in order, a promoter, silk gene repeats, GFP, a His tag, and a terminator, may at once be envisioned one skilled in the art. See FIG. 23 for an example.

FIG. 22 depicts a spider silk production system constructed using the BioBrick assembly standard. 'P' is a Lac Promoter and Ribosome Binding site. atgB1 is one repeat of spider silk subunit of the MaSp2 gene from Argiope aurantia containing a methionine (atg). 'B13' are 13 repeats of 'B' are spider silk subunits of the MaSp2 gene from A. aurantia. 'HT' is the 10×His-tag with a double stop codon. 'B0015' is a double terminator BBa_B0015 (figure not to scale).

Figure 23:
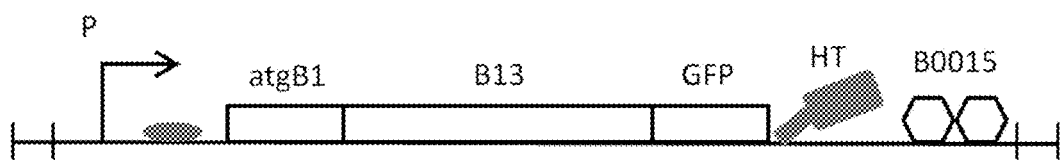
FIG. 23 depicts a spider silk production and monitoring system with GFP fused on the C-terminal end of the spider silk.

FIG. 23 depicts a spider silk production and monitoring system with GFP fused on the C-terminal end of the spider silk (figure not to scale).

Media Preparation:

All initial growth experiments during cloning were carried out in standard LB media (Sambrook and Russel 2001) with 34 µg/mL of chloramphenicol (Acros Organics, Fair Lawn, N.J.) and/or 5-µg/mL Kanamycin (Gold Biotechnology Inc., St Louis, Mo.) at 37° C. on an orbital shaker table at 220 rpm.

Bioreactor Scale-Up:

Spider silk producing E. coli strains (with and without tRNAs) were grown overnight as a seed culture in 200 mL High Express medium+Glucose in 500 mL capacity Erlenmeyer flask on a shaker table at 220 rpm, 37° C. with 34 µg mL$^{-1}$ chloramphenicol. Seed culture was added to a 10 L Winpact Bioreactor and Fermentor (GMI, Inc., Ramsey, Minn.). Media used in bioreactor were modified based on Dong et al. 2012 (Chen, Brown et al. 2012). Bioreactor medium consisted of 10 g/L Hy-Express™ System II (Sheffield Bio-Science, Beloit, Wis.), 5 g/L Hy-Yest™ 444 (Sheffield Bio-Science, Beloit, Wis.), 2 g/L Lactose, 2.2 g/L Glucose, 16 g/L Glycerol (Amresco, Solon, Ohio), 7.1 g/L $Na_2HPO_4$, 6.8 g/L $KH_2PO_4$, and 3.3 g/L $(NH_4)_2SO_4$. Additional, trace elements were added as mentioned in Dong et al. 2012 (Chen, Brown et al. 2012). A dissolved $O_2$ level of 40% was controlled and monitored by gassing with air, 02, and agitation. $NH_4OH$ was used to keep pH at 6.0 and Himar FGK antifoam (Jeneil Biotech Inc., Saukville, Wis.) was added automatically via controller during fermentation. Protein expression was auto-induced when culture exhausted glucose source, and Lac-inducible promoter would be completely available for transcription by RNA polymerase. Culture was harvested approximately 20-24 hr after seeding using a CEPA Z41 continuous flow centrifuge (Eppendorf, Hamburg, Germany) and cell pellet was immediately stored at −80° C.

Protein Purification:

Approximately 50 g of wet biomass from the bioreactor run was resuspended in a binding buffer and sonicated for approximately 10 min. *Lysosome* was added to the slurry and allowed to sit at room temperature for 10 min. A Urea solution was then added to the slurry and further sonicated for 10 min. The lysed cells slurry was centrifuged at 8500 rpm for 60 min. The supernatant fraction was run through an AKTA Avant system (GE Healthcare Biosciences, Pittsburgh, Pa.) with 5 mL HisTrap FF crude nickel column (GE Healthcare Biosciences, Pittsburgh, Pa.) for spider silk protein purification. Non-specifically bound protein, flow through, and lysed cell debris was saved for analysis.

PAGE/Western:

Proteins were mixed with loading buffer, and heat treated for 1-3 min. 30 μL of protein and buffer were loaded into precast 4-20% Precise Protein gels (Thermo Scientific Inc., Rockford, Ill.). Precision Plus Protein™ marker (Bio-Rad, Hercules, Calif.) was used to visualize protein propagation. For visualization, gels were stained with Bio-Safe Coomassie Stain for 1 hour (Bio-Rad, Hercules, Calif.) and de-stained overnight. For Western Blot analysis, proteins were electroblotted from gel to nitrocellulose membrane (Bio-rad, Hercules, Calif.) and blocked with 5% non-fat milk TBS-Tween-20 for 30-60 min. Primary antibody, Anti-6×HIS EPITOPE TAG (MOUSE) Monoclonal Antibody (Rockland Immunochemicals Inc., Gilbertsville, Pa.) was used in a 1:4000 ratio. Membrane was then washed 3 times with TBS-Tween-20 and blocked with blocking solution. Secondary antibody anti-Mouse IgG H&L ab6729 1:4000 (Abcam Inc, Cambridge, Mass.) was added to $2^{nd}$ block for 30 min, washed 3 times with TBS-Tween-20. 1-Step NBT/BCIP substrate (Thermo Fisher Scientific Inc, Rockford, Ill.) was added and chemiluminescence was allowed to occur for 10 minutes.

Fluorescent Studies:

Cultures were grown in LB media with required antibiotics (except for *E. coli* only control). 34 μg/mL chloramphenicol and 50 μg/mL kanamycin were used in this study. 0.1 mM IPTG was added at time=0 and cultures were allowed to grow overnight (~15 hours) in an orbital shaker at 220 rpm, 37° C. Cultures were measured at an $OD_{600}$ and dilutions were carried out with 0.15M NaCl to 1.5 mL volume to ensure each culture had approximately the same $OD_{600}$=0.5. Dilutions were centrifuged at 10,000×g for 5 minutes and supernatant was removed. 0.8 mL of 0.15M NaCl was then used to resuspended the cells. 200 μL was loaded into 3 separate wells in a black microtider 96 well plate for each sample. Fluorescence analysis was then conducted using a Biotech Senergy 2 plate reader with an excitation of approximately 395 nm and emission of 509 nm for GFP. Filter wheels used in study were: excitation 360/40 and emission 528/20. Fluorescence values for BL21 cells were subtracted from the values obtained from samples containing GFP. Triplicate values were averaged and plotted.

LB agar plates containing appropriate antibiotics were surface coated with 0.1 mM IPTG. Cells containing the silk-GFP construct were applied to the surface of the plate. Plates were placed in a 37° C. incubator overnight. Plates were then placed on a UV box and photographed.

Bioreactor Growth:

After 24 hours post inoculation, the $OD_{600}$, of the patgB14HT (in BL21) in a bioreactor operated in batch mode, reached approximately 44. The patgB14HT+tRNA constructs in BL21 reached an $OD_{600}$ of approximately 43. Comparing the $OD_{600}$ between the two different strains suggests that the expression of tRNAs does not inhibit the growth of *E. coli*.

Some of the bacterial pellet was mini-prepped and digested with EcoRI and PstI to see if the plasmid patgB14HT was still present and the results showed an insert band at ~3.4 kbp and vector band at ~2.1 kbp (not shown). This confirmed the maintenance of the expression plasmid.

Figure 24:
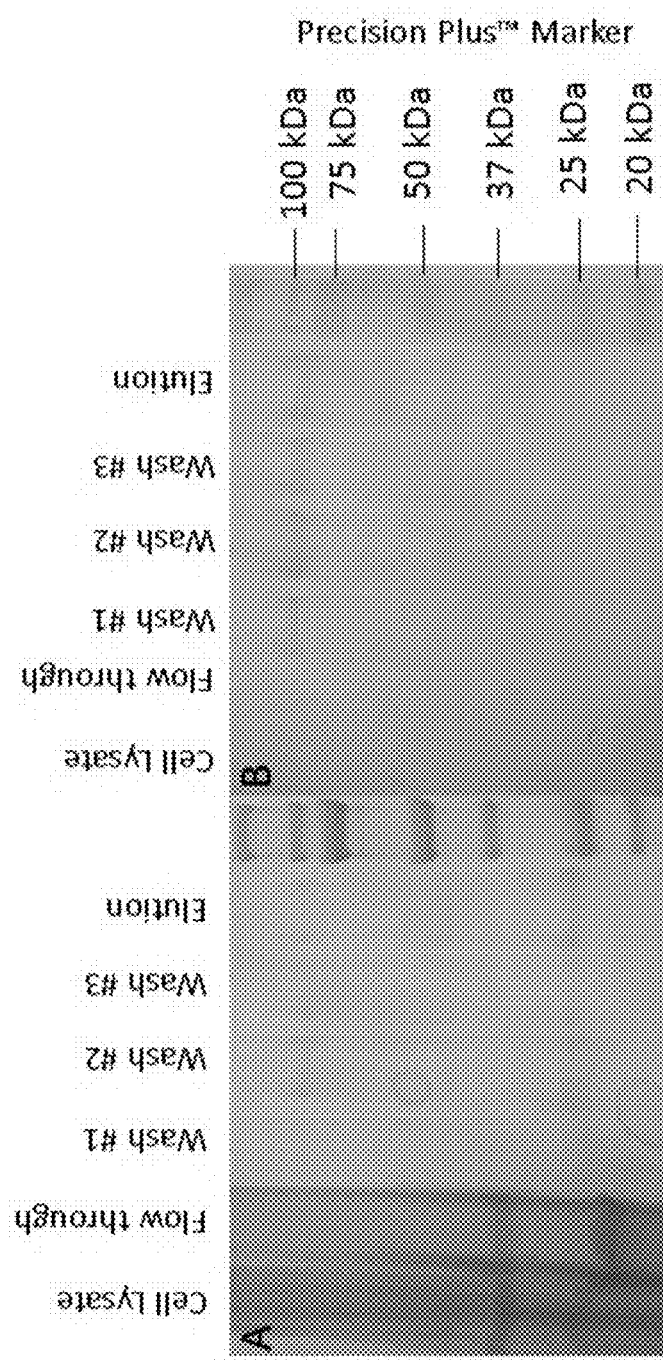
FIG. 24 depicts The SDS polyacrylamide gel for patgB14HT.

Analysis of Spider Silk Protein Production:

The SDS polyacrylamide gel for patgB14HT (FIG. 24A) showed bands slightly greater than 85.7 kDa in elution fraction, and wash fraction. The corresponding immunoblot (FIG. 24B) showed the presence of a band in elution fraction and the wash fractions. The immunoblot did not show the protein of interest in the flow through or cell lysate fractions. For both FIGS. 24A and 24B, the columns left to right are as follows: cell lysate, flow through, wash fractions, elution fraction, and Precision Plus Protein™ Marker.

Figure 25:
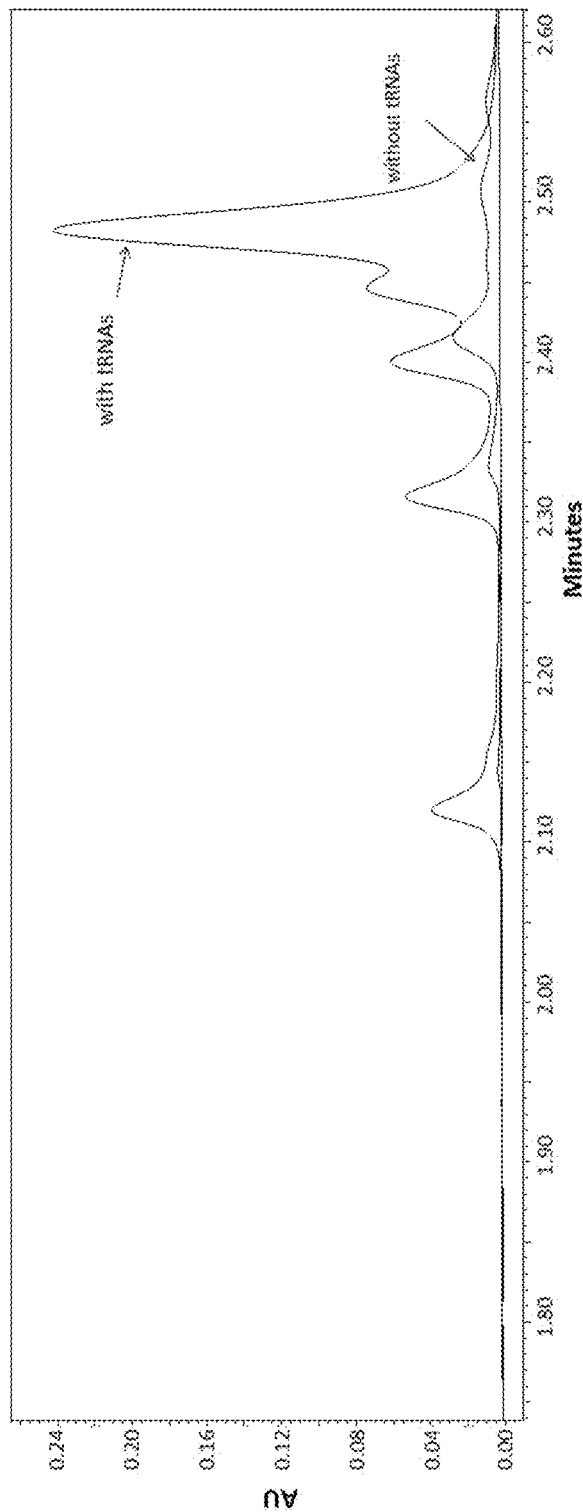
FIG. 25 depicts the results of upregulating tRNAs in an exemplary expression system.

In order to compare the patgB14HT with and without tRNAs, HPLC was carried out as demonstrated in FIG. 25. It was seen that when tRNAs were expressed the overall yield of spider silk was increased approximately 20 fold. FIG. 25 shows HPLC on elution fractions from patgB14HT and patgB14HT with tRNAs. The construct that has tRNAs demonstrates increased production of spider silk. Cells that contain overexpressed tRNAs demonstrate increased production of spider silk. Full-length spider silk protein is observed between 2.45 and 2.55 min.

Fluorescent Studies:

To further demonstrate that tRNAs increase overall spider silk production, spider silk was fused to GFP and fluorescence was measured.

Figure 26:
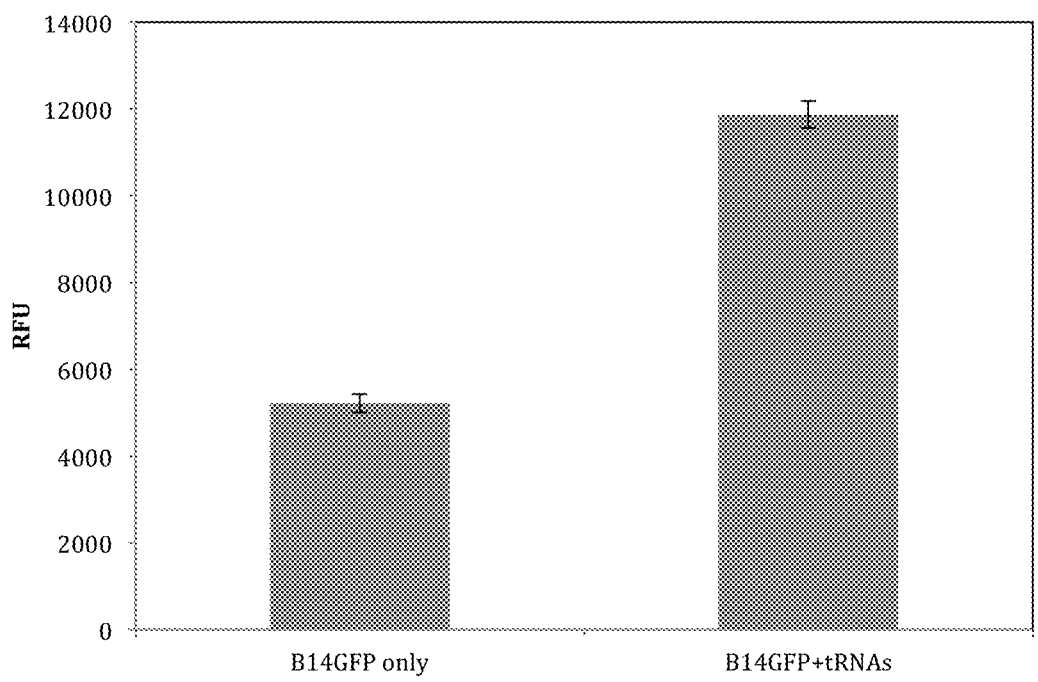
FIG. 26 depicts the difference in fluorescence levels between strains containing patgB14GFPHT with and without tRNA upregulation.

FIG. 26 shows the difference in fluorescence levels between strains containing patgB14GFPHT with and without tRNAs. With the addition of the tRNA plasmid it is clear that the total level of fluorescence increased. This demonstrates that the additional tRNAs help in transcription and subsequent translation to protein. The advantage of having GFP at the C-terminal means that only fully transcribed DNA sequences will fluoresce. Furthermore the 10× Histag is on the C-terminal after the GFP so only fully transcribed DNA will produce protein that can be purified. Referring again to FIG. 26, pRJP2 and pRJP2+pRPAR1 relative fluorescence units (RFU) are shown. Excitation was carried out at 360/40 nm and emission 528/20 nm. Peaks represent emission values.

Figure 27:
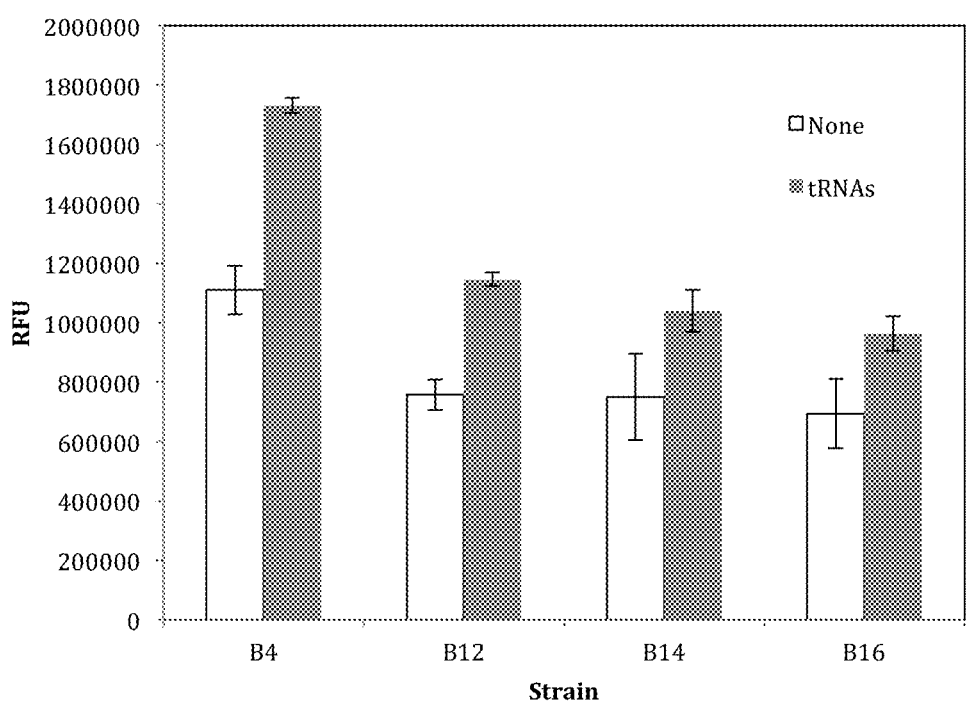
FIG. 27 depicts protein expression as fluorescence levels for samples with and without tRNA upregulation.

Additional studies were carried out on different spider silk repeat numbers with and without tRNAs. From FIG. 27 it can be seen that fluorescence levels for samples without tRNAs are lower than those samples that contain tRNAs. This demonstrates that additional tRNAs increase overall spider silk production. Referring again to FIG. 27, different repeats of spider silk subunit were fused with GFP, on the C-terminal end. Each repeat was tested for fluorescence with and without tRNAs.

Example 9

Sequentially Building a Spider Silk Protein

In embodiments, the preset disclosure provides methods for sequentially constructing a recombinant nucleotide sequences that encodes at least one spider silk protein. The construction of an exemplary expression vector for expressing synthetic spider silk proteins was carried out using the spider silk encoding sequences in SEQ ID NO:16 and SEQ ID NO:17. Recombinant nucleotide sequences were sequentially lengthened using molecular biological techniques including restriction endonuclease digestion of DNA, DNA ligation, DNA transformation, and DNA purification.

Figure 28:
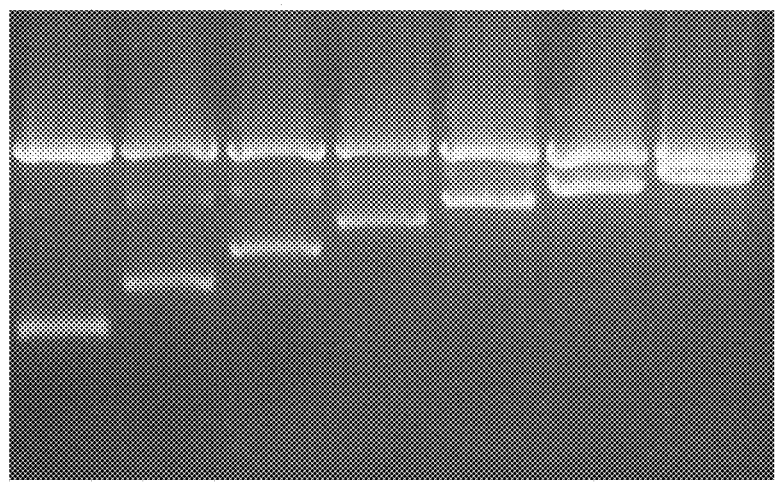
FIG. 28 depicts an agarose DNA gel with lanes 1-7 showing cut DNA of a sequentially built up nucleotide sequence constructed from units of SEQ ID NO:16.

Referring now to FIG. 28, there is shown an agarose DNA gel with lanes 1-7 representing cut DNA of a sequentially built up nucleotide sequence with sizes of 462 bp, 679 bp, 896 bp, 1113 bp, 1330 bp, 1547 bp, and 1764 bp respectively, which was constructed from units of SEQ ID NO:16. Each lane has a band of the same size (~2.1 kb) that is the plasmid backbone pSB1C3.

Figure 29:
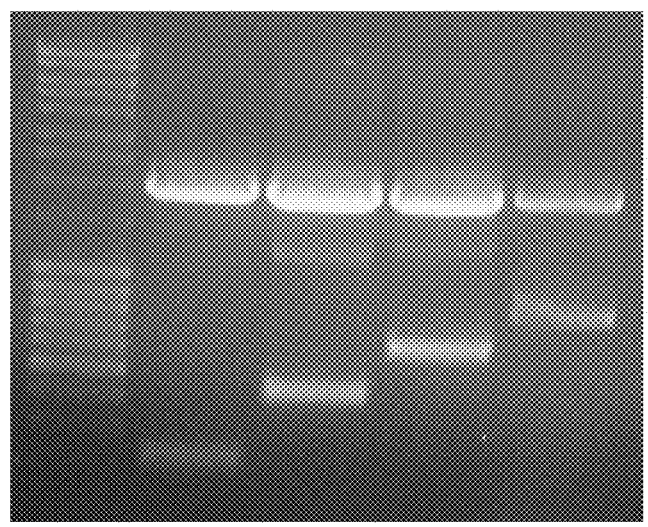
FIG. 29 depicts an agarose DNA gel with lanes 1-5 representing a sequentially built up nucleotide sequence constructed from units of SEQ ID NO:17.

Referring now to FIG. 29, there is shown an agarose DNA gel with lanes 1-5 representing: Mass ruler DNA ladder, and sequentially built up nucleotide sequences having sizes of 245 bp, 462 bp, 679 bp, and 896 bp respectively, which were construct from units of SEQ ID NO:17. Each lane has a band of the same size (~2.1 kb), which is the plasmid backbone pSB1C3.

SEQUENCE LISTING

```
<160> NUMBER OF SEQ ID NOS: 27

<210> SEQ ID NO 1
<211> LENGTH: 1052
<212> TYPE: DNA
<213> ORGANISM: Artificial Sequence
<220> FEATURE:
<223> OTHER INFORMATION: Some of the artificial sequences are based, at
      least in part, on sequences from common spiders.  Please see the
      specification for the complete explanation of the origin of the
      sequences.

<400> SEQUENCE: 1
aagcttcata tgaccggtgg tgcaggtcag ggtggttatg gtggtctggg tagccagggt      60
gccggtcgtg gtggactggg tggtcaaggt gctggtgcag cagcagctgc cgcagcagca     120
ggcggtgcag gccaaggcgg atatggcgga ctgggttcac agggtgcagg ccgtggcggt     180
ttaggtggtc aaggcgcagg cgctgctgca gccgcagcgg cagcagctgg ccaaggtggc     240
tatggtggct taggctcaca gggtggcggt gctggacagg gtggatacgg tggccttggc     300
agtcaaggtg cgggtcgcgg tggtttaggc ggtcagggtg cgggtcgcgc tgctgcagct     360
gcggcagcgg gtggtgctgg gcaaggcggt tacggtggat taggtagcca aggtgcagga     420
cgcggaggtc ttggtggaca gggtgctggc gctgctgcgg cagcagcagc cgctggggt     480 gctggtcaag ggggttatgg cggtttagga tctcagggtg cgggacgggg tggtctggga     540
gggcaagggg caggcgcagc agcagcggca gctgcagccg gtggtgccgg acaagggga     600 tatggggtc ttggctccca aggcgctggt cgtggcggtc ttggaggcca aggtgccggt     660
gccgctgcag cggctgctgc tgcagcgggt caagggggat acggtggtct gggatcacaa     720
ggtggtggcg cagggcaagg tgggtatggg ggtttaggtt cgcaaggtgc tggccgtggg     780
ggactgggag gacagggtgc cggtgcggca gccgctgcag ctgctgcggg tggcgctggt     840
cagggtggct atggcggatt gggctctcaa ggggcaggtc ggggtggctt gggaggacaa     900
ggtgcgggtg cagccgctgc ggcagctgcc gctggcggag caggccaggg tggctacggt     960 ggactggggtt cccaaggtgc gggaagaggt ggcttgggtg gccagggtgc aggggcagcg    1020
gctgcagcgg cagcagcctc cggaggggat cc                                  1052

<210> SEQ ID NO 2
<211> LENGTH: 350
<212> TYPE: PRT
<213> ORGANISM: Artificial Sequence
<220> FEATURE:
<223> OTHER INFORMATION: Synthetic sequences based on spider sequences
```

<400> SEQUENCE: 2

Lys Leu His Met Thr Gly Gly Ala Gly Gln Gly Gly Tyr Gly Gly Leu
1               5                   10                  15

Gly Ser Gln Gly Ala Gly Arg Gly Gly Leu Gly Gly Gln Gly Ala Gly
            20                  25                  30

Ala Ala Ala Ala Ala Ala Ala Gly Gly Ala Gly Gln Gly Gly Tyr
        35                  40                  45

Gly Gly Leu Gly Ser Gln Gly Ala Gly Arg Gly Gly Leu Gly Gly Gln
    50                  55                  60

Gly Ala Gly Ala Ala Ala Ala Ala Ala Ala Gly Gln Gly Gly
65                  70                  75                  80

Tyr Gly Gly Leu Gly Ser Gln Gly Gly Ala Gly Gln Gly Gly Tyr
            85                  90                  95

Gly Gly Leu Gly Ser Gln Gly Ala Gly Arg Gly Gly Leu Gly Gly Gln
            100                 105                 110

Gly Ala Gly Ala Ala Ala Ala Ala Ala Gly Gly Ala Gly Gln
        115                 120                 125

Gly Gly Tyr Gly Gly Leu Gly Ser Gln Gly Ala Gly Arg Gly Gly Leu
    130                 135                 140

Gly Gly Gln Gly Ala Gly Ala Ala Ala Ala Ala Ala Ala Gly Gly
145                 150                 155                 160

Ala Gly Gln Gly Gly Tyr Gly Gly Leu Gly Ser Gln Gly Ala Gly Arg
                165                 170                 175

Gly Gly Leu Gly Gly Gln Gly Ala Gly Ala Ala Ala Ala Ala Ala
            180                 185                 190

Ala Gly Gly Ala Gly Gln Gly Gly Tyr Gly Gly Leu Gly Ser Gln Gly
        195                 200                 205

Ala Gly Arg Gly Gly Leu Gly Gly Gln Gly Ala Gly Ala Ala Ala Ala
    210                 215                 220

Ala Ala Ala Ala Ala Gly Gln Gly Gly Tyr Gly Gly Leu Gly Ser Gln
225                 230                 235                 240

Gly Gly Gly Ala Gly Gln Gly Gly Tyr Gly Gly Leu Gly Ser Gln Gly
            245                 250                 255

Ala Gly Arg Gly Gly Leu Gly Gly Gln Gly Ala Gly Ala Ala Ala Ala
            260                 265                 270

Ala Ala Ala Ala Gly Gly Ala Gly Gln Gly Gly Tyr Gly Gly Leu Gly
        275                 280                 285

Ser Gln Gly Ala Gly Arg Gly Gly Leu Gly Gln Gly Ala Gly Ala
    290                 295                 300

Ala Ala Ala Ala Ala Ala Gly Gly Ala Gly Gln Gly Gly Tyr Gly
305                 310                 315                 320

Gly Leu Gly Ser Gln Gly Ala Gly Arg Gly Gly Leu Gly Gly Gln Gly
            325                 330                 335

Ala Gly Ala Ala Ala Ala Ala Ala Ala Ala Ser Gly Gly Asp
        340                 345                 350

<210> SEQ ID NO 3
<211> LENGTH: 1049
<212> TYPE: DNA
<213> ORGANISM: Artificial Sequence
<220> FEATURE:
<223> OTHER INFORMATION: Synthetic sequences based on spider sequences

<400> SEQUENCE: 3
aagcttcata tgaccggtcc gggtcagcag ggtccgggtg gttatggtcc tggccagcag      60

```
ggaccgagcg gtccgggtag tgcagcagca gctgcagcag ccgcaggccc tggtcagcaa      120
ggccctggtg gatatggacc aggccaacag ggtcctggcg gatacggtcc tggtcaacaa      180
ggtccgtcag gtccgggttc agccgcagcg gctgctgccg cagcaggtcc aggtggctac      240
ggaccgggtc aacagggacc cggtgggtac ggaccaggac agcaagggcc aggcggttat      300
ggccctggac aacaagggcc tagtggtcct ggttctgcag cggcagccgc tgcggcagct      360
ggtccgggac agcaaggacc cggtggatac ggtcccggtc agcagggacc tggcggttac      420
ggacccggac aacagggtcc atctggtcct ggtagcgcag ccgcagcagc agcggctgca      480
ggtccaggac aacaaggtcc tggtgggtat ggtccagggc agcaaggtcc gagtggtcca      540
ggctctgcgg cagcggcagc agcagcagcg ggacctggtc aacagggtcc aggggatat      600 ggcccaggtc agcaaggacc gggtggctat gggccaggtc aacaaggccc tagcggtccg      660
ggatctgccg cagctgcagc ggcagcggca ggtcctggcg gttatggacc aggtcagcag      720
ggtcccggtg gctacggtcc cggacaacaa ggcccagggg gttacggacc tggccagcaa      780
ggtccttctg gaccgggaag cgctgcagcc gcagcagctg cagccggtcc aggccagcaa      840
gggcctgggg gttacggtcc gggtcagcaa ggcccaggcg gatacggtcc aggacaacag      900
ggaccaagtg gtccgggatc agcagccgct gccgcagcgg cagccggtcc cggtcaacaa      960
ggacctggtg gctacggtcc tgggcaacag ggtcctagcg gtccagggtc agcagcagca     1020
gccgcagctg cagcatccgg aggggatcc                                        1049

<210> SEQ ID NO 4
<211> LENGTH: 349
<212> TYPE: PRT
<213> ORGANISM: Artificial Sequence
<220> FEATURE:
<223> OTHER INFORMATION: Synthetic sequences based on spider sequences

<400> SEQUENCE: 4

Lys Leu His Met Thr Gly Pro Gly Gln Gln Gly Pro Gly Gly Tyr Gly
 1               5                  10                  15

Pro Gly Gln Gln Gly Pro Ser Gly Pro Gly Ser Ala Ala Ala Ala Ala
                20                  25                  30

Ala Ala Ala Gly Pro Gly Gln Gln Gly Pro Gly Gly Tyr Gly Pro Gly
            35                  40                  45

Gln Gln Gly Pro Gly Gly Tyr Gly Pro Gly Gln Gln Gly Pro Ser Gly
        50                  55                  60

Pro Gly Ser Ala Ala Ala Ala Ala Ala Ala Gly Pro Gly Gly Tyr
 65                  70                  75                  80

Gly Pro Gly Gln Gln Gly Pro Gly Gly Tyr Gly Pro Gly Gln Gln Gly
                 85                  90                  95

Pro Gly Gly Tyr Gly Pro Gly Gln Gln Gly Pro Ser Gly Pro Gly Ser
            100                 105                 110

Ala Ala Ala Ala Ala Ala Ala Gly Pro Gly Gln Gln Gly Pro Gly
        115                 120                 125

Gly Tyr Gly Pro Gly Gln Gln Gly Pro Gly Gly Tyr Gly Pro Gly Gln
    130                 135                 140

Gln Gly Pro Ser Gly Pro Gly Ser Ala Ala Ala Ala Ala Ala Ala
145                 150                 155                 160

Gly Pro Gly Gln Gln Gly Pro Gly Gly Tyr Gly Pro Gly Gln Gln Gly
                165                 170                 175

Pro Ser Gly Pro Gly Ser Ala Ala Ala Ala Ala Ala Ala Gly Pro
```

```
            180                 185                 190
Gly Gln Gln Gly Pro Gly Gly Tyr Gly Pro Gly Gln Gln Gly Pro Gly
            195                 200                 205
Gly Tyr Gly Pro Gly Gln Gln Gly Pro Ser Gly Pro Gly Ser Ala Ala
            210                 215                 220
Ala Ala Ala Ala Ala Gly Pro Gly Gly Tyr Gly Pro Gly Gln Gln
225                 230                 235                 240
Gly Pro Gly Gly Tyr Gly Pro Gly Gln Gln Gly Pro Gly Gly Tyr Gly
                245                 250                 255
Pro Gly Gln Gln Gly Pro Ser Gly Pro Gly Ser Ala Ala Ala Ala
            260                 265                 270
Ala Ala Ala Gly Pro Gly Gln Gln Gly Pro Gly Gly Tyr Gly Pro Gly
            275                 280                 285
Gln Gln Gly Pro Gly Gly Tyr Gly Pro Gly Gln Gln Gly Pro Ser Gly
            290                 295                 300
Pro Gly Ser Ala Ala Ala Ala Ala Ala Ala Gly Pro Gly Gln Gln
305                 310                 315                 320
Gly Pro Gly Gly Tyr Gly Pro Gly Gln Gln Gly Pro Ser Gly Pro Gly
                325                 330                 335
Ser Ala Ala Ala Ala Ala Ala Ala Ser Gly Gly Asp
            340                 345
```

<210> SEQ ID NO 5
<211> LENGTH: 1205
<212> TYPE: DNA
<213> ORGANISM: Artificial Sequence
<220> FEATURE:
<223> OTHER INFORMATION: Synthetic sequences based on spider sequences

<400> SEQUENCE: 5

```
aagcttcata tgaccggtgg tgccggtggt tatggtcgtg gtgctggtgc gggtgccggt      60
gcagcagctg gtgccggtgc tggcgcaggc ggttatggtg gtcagggtgg ctacggtgcc     120
ggtgccggtg ctggtgccgc agccgcagcg ggtgcgggtg caggcggtgc tggcggttat     180
ggcagaggtg ctggggctgg tgcaggcgct gcagccggtg cgggtgctgg tgcgggtgga     240
tatggtggcc agggtggtta tggcgctggc gcaggggcag gcgcagcagc agcagctggg     300
gcaggcgcag gcggtgccgg tggctatgga gcgggagccg gtgccggtgc aggggcagca     360
gcgggtgctg gtgccggtgc aggggggttat ggtggccaag gcggatatgg tgcgggtgca     420
ggcgctggtg cagcagcagc cgctggtgcc ggtgccggtg gtgcgggtgg ctacggaaga     480
ggtgcgggtg ccggtgccgg tgctgcagcg ggtgcgggtg cgggtgccgg tggttatggc     540
ggtcagggtg gtatggtgc gggtgctggt gcaggcgcag ctgcagccgc tggtgctggt     600
gcaggcggag ccggtggata tggccgaggt gctggcgcag gcgctggcgc tgctgctggt     660
gccggtgcgg gtgctggggg atacggtggt caagggggtt atggtgcggg tgccggtgcg     720
ggtgcagccg cagcagctgg tgcgggtgcg ggtggtgcag gggatatgg ccgtggtgcc     780
ggtgctggtg cgggtgctgc agccggtgct ggggcagggg ctggcggtta tggggggtcaa     840
ggcggttatg cgctggtgc tggtgctggg gctgccgcag cagccggtgc tggtgctggc     900
ggtgcgggtg gttacggtcg gggagctggc gctggtgctg gcgcagcagc gggtgccggt     960
gctggtgccg gtggctacgg tggacaaggt ggctatggtg ccggtgcagg cgcaggggct    1020
gcagccgcag ccggtgccgg tgccggtggc gctgggggtt atggtcgcgg agcgggtgca    1080
ggcgcaggcg cagccgctgg cgctggtgcg ggtgctggcg gttatggtgg acaaggggggt    1140
```

```
tatgggctg gtgctggcgc aggggcagct gctgcagcgg gtgctggcgc ttccggaggg    1200
gatcc                                                              1205
```

<210> SEQ ID NO 6
<211> LENGTH: 401
<212> TYPE: PRT
<213> ORGANISM: Artificial Sequence
<220> FEATURE:
<223> OTHER INFORMATION: Synthetic sequences based on spider sequences

<400> SEQUENCE: 6

Lys Leu His Met Thr Gly Gly Ala Gly Gly Tyr Gly Arg Gly Ala Gly
1               5                   10                  15

Ala Gly Ala Gly Ala Ala Ala Gly Ala Gly Ala Gly Ala Gly Gly Tyr
            20                  25                  30

Gly Gly Gln Gly Gly Tyr Gly Ala Gly Ala Gly Ala Gly Ala Ala Ala
        35                  40                  45

Ala Ala Gly Ala Gly Ala Gly Ala Gly Gly Tyr Gly Arg Gly Ala
    50                  55                  60

Gly Ala Gly Ala Gly Ala Ala Ala Gly Ala Gly Ala Gly Ala Gly Gly
65                  70                  75                  80

Tyr Gly Gly Gln Gly Gly Tyr Gly Ala Gly Ala Gly Ala Gly Ala Ala
                85                  90                  95

Ala Ala Ala Gly Ala Gly Ala Gly Ala Gly Gly Tyr Gly Arg Gly
            100                 105                 110

Ala Gly Ala Gly Ala Gly Ala Ala Ala Gly Ala Gly Ala Gly Ala Gly
            115                 120                 125

Gly Tyr Gly Gly Gln Gly Gly Tyr Gly Ala Gly Ala Gly Ala Gly Ala
        130                 135                 140

Ala Ala Ala Ala Gly Ala Gly Ala Gly Ala Gly Gly Tyr Gly Arg
145                 150                 155                 160

Gly Ala Gly Ala Gly Ala Gly Ala Ala Ala Gly Ala Gly Ala Gly Ala
                165                 170                 175

Gly Gly Tyr Gly Gly Gln Gly Gly Tyr Gly Ala Gly Ala Gly Ala Gly
            180                 185                 190

Ala Ala Ala Ala Ala Gly Ala Gly Ala Gly Ala Gly Gly Tyr Gly
        195                 200                 205

Arg Gly Ala Gly Ala Gly Ala Gly Ala Ala Ala Gly Ala Gly Ala Gly
        210                 215                 220

Ala Gly Gly Tyr Gly Gly Gln Gly Gly Tyr Gly Ala Gly Ala Gly Ala
225                 230                 235                 240

Gly Ala Ala Ala Ala Ala Gly Ala Gly Ala Gly Gly Ala Gly Gly Tyr
                245                 250                 255

Gly Arg Gly Ala Gly Ala Gly Ala Gly Ala Ala Ala Gly Ala Gly Ala
            260                 265                 270

Gly Ala Gly Gly Tyr Gly Gly Gln Gly Gly Tyr Gly Ala Gly Ala Gly
        275                 280                 285

Ala Gly Ala Ala Ala Ala Gly Ala Gly Ala Gly Ala Gly Gly
    290                 295                 300

Tyr Gly Arg Gly Ala Gly Ala Gly Ala Gly Ala Ala Ala Gly Ala Gly
305                 310                 315                 320

Ala Gly Ala Gly Gly Tyr Gly Gly Gln Gly Gly Tyr Gly Ala Gly Ala
                325                 330                 335

Gly Ala Gly Ala Ala Ala Ala Ala Gly Ala Gly Ala Gly Gly Ala Gly

```
                340             345             350
Gly Tyr Gly Arg Gly Ala Gly Ala Gly Ala Ala Gly Ala
            355             360             365

Gly Ala Gly Ala Gly Gly Tyr Gly Gly Gln Gly Gly Tyr Gly Ala Gly
        370                 375                 380

Ala Gly Ala Gly Ala Ala Ala Ala Gly Ala Gly Ala Ser Gly Gly
385                 390                 395                 400

Asp

<210> SEQ ID NO 7
<211> LENGTH: 1065
<212> TYPE: DNA
<213> ORGANISM: Artificial Sequence
<220> FEATURE:
<223> OTHER INFORMATION: Synthetic sequences based on spider sequences

<400> SEQUENCE: 7
aagcttcata tgggatcaac cggtcccggg ggtccgggtg gttatggtcc tggtggtagt      60
ggtccaggtg gctatggacc gggtggttcc ggtccaggcg gttatggccc tggcggttca     120
ggtccgggtg gatacggacc aggtggcagc ggtccgagtg gtccgggtag tgcagcagca     180
gcagccgcag ctgcaggtcc aggggatat ggtccagggg gtagcggacc tggcggttat     240
gggccaggtg gctctggccc tggtggatat ggcccaggcg gaagtggccc aggtggttac     300
ggacctgggg gatcaggacc aggcggttac ggtccgggtg gctcaggtcc tagcggtccg     360
ggttcagccg cagcggcagc agcagcggca ggaccgggtg gctatgggcc aggggggttcg     420 ggacctggtg gttatggacc tggcggaagc ggtcctgggg gttacggtcc aggtggaagt     480
ggaccgtcag gtccaggtag cgcagctgcc gctgcagccg cagcaggtcc aggtgggtac     540
ggtcctggtg gttctggacc gggtgggtat ggtccgggtg gaagcggacc gggtggatat     600
ggccctgggg gatctggtcc tggcggatat ggacctggtg gtcgggacc aggggggatac     660 ggaccgggtg gtagtggccc caggcggatac ggtcctggcg gtagcggtcc atcaggtccg     720
ggatctgctg ctgctgcggc agctgcagcc ggaccagggg gttatggacc aggtggttca     780
ggaccaggtg gctacggtcc aggcggtagt gggcctgggg gatatggtcc gggtggctct     840
gggcctggcg gttacggacc tggcggtagt ggaccgggtg gttatggccc aggtggctcc     900
ggtccgggtg gtatggggcc aggtggatct gggccaggcg gttatggtcc aggggggatcg     960 ggtccaggtg gatatgggcc aggtggttca ggtccatctg gtccgggttc cgcagctgca    1020
gccgcagccg cagcttccgg agggcccgat atcctcgagg gatcc                    1065

<210> SEQ ID NO 8
<211> LENGTH: 355
<212> TYPE: PRT
<213> ORGANISM: Artificial Sequence
<220> FEATURE:
<223> OTHER INFORMATION: Synthetic sequences based on spider sequences

<400> SEQUENCE: 8

Lys Leu His Met Gly Ser Thr Gly Pro Gly Gly Pro Gly Gly Tyr Gly
1               5                   10                  15

Pro Gly Gly Ser Gly Pro Gly Gly Tyr Gly Pro Gly Gly Ser Gly Pro
                20                  25                  30

Gly Gly Tyr Gly Pro Gly Gly Ser Gly Pro Gly Gly Tyr Gly Pro Gly
            35                  40                  45

Gly Ser Gly Pro Ser Gly Pro Gly Ser Ala Ala Ala Ala Ala Ala Ala
```

```
                50                   55                   60
Ala Gly Pro Gly Gly Tyr Gly Pro Gly Gly Ser Gly Pro Gly Gly Tyr
 65                  70                  75                  80

Gly Pro Gly Gly Ser Gly Pro Gly Gly Tyr Gly Pro Gly Gly Ser Gly
                 85                  90                  95

Pro Gly Gly Tyr Gly Pro Gly Gly Ser Gly Pro Gly Gly Tyr Gly Pro
                100                 105                 110

Gly Gly Ser Gly Pro Ser Gly Pro Gly Ser Ala Ala Ala Ala Ala Ala
                115                 120                 125

Ala Ala Gly Pro Gly Gly Tyr Gly Pro Gly Gly Ser Gly Pro Gly Gly
            130                 135                 140

Tyr Gly Pro Gly Gly Ser Gly Pro Gly Gly Tyr Gly Pro Gly Gly Ser
145                 150                 155                 160

Gly Pro Ser Gly Pro Gly Ser Ala Ala Ala Ala Ala Ala Ala Ala Gly
                165                 170                 175

Pro Gly Gly Tyr Gly Pro Gly Gly Ser Gly Pro Gly Gly Tyr Gly Pro
                180                 185                 190

Gly Gly Ser Gly Pro Gly Gly Tyr Gly Pro Gly Gly Ser Gly Pro Gly
            195                 200                 205

Gly Tyr Gly Pro Gly Gly Ser Gly Pro Gly Gly Tyr Gly Pro Gly Gly
        210                 215                 220

Ser Gly Pro Gly Gly Tyr Gly Pro Gly Gly Ser Gly Pro Ser Gly Pro
225                 230                 235                 240

Gly Ser Ala Ala Ala Ala Ala Ala Ala Ala Gly Pro Gly Gly Tyr Gly
                245                 250                 255

Pro Gly Gly Ser Gly Pro Gly Gly Tyr Gly Pro Gly Gly Ser Gly Pro
                260                 265                 270

Gly Gly Tyr Gly Pro Gly Gly Ser Gly Pro Gly Gly Tyr Gly Pro Gly
            275                 280                 285

Gly Ser Gly Pro Gly Gly Tyr Gly Pro Gly Gly Ser Gly Pro Gly Gly
        290                 295                 300

Tyr Gly Pro Gly Gly Ser Gly Pro Gly Gly Tyr Gly Pro Gly Gly Ser
305                 310                 315                 320

Gly Pro Gly Gly Tyr Gly Pro Gly Gly Ser Gly Pro Ser Gly Pro Gly
                325                 330                 335

Ser Ala Ala Ala Ala Ala Ala Ala Ser Gly Gly Pro Asp Ile Leu
                340                 345                 350

Glu Gly Ser
        355

<210> SEQ ID NO 9
<211> LENGTH: 1181
<212> TYPE: DNA
<213> ORGANISM: Artificial Sequence
<220> FEATURE:
<223> OTHER INFORMATION: Synthetic sequences based on spider sequences

<400> SEQUENCE: 9
aagcttcata tgaccggtgg ttatccgggt ggctatcctg gtggtcaggg tgcaggtccg      60
ctgggtggtg ttccgctggt tagccagagc ctggataatc tgggtggtgg tggtgcacag    120
gcaggtctga ttagccgtgt tgcaaatgca ctggcaaata ccagcaccct gcgtgcagtt    180
ctgcgtcgtg gtgttagcca gaataccgtt aataatgttg ttcagcgtac cgttcagagc    240
ctggccaata ccctgggtgt tgatggtaat aatctggcac gtattgcaag ccaggcaatt    300
```

```
agccaggttc cggcaggtag cgataccaat gcctatgcac aggcactgag caccgcaaat    360
ctggttacag gtggtattct gaatgaacgc aatattgata gcctgggtag ccgtgttctg    420
agcgcagttc tgaatggtgt tagcagcgca gcacagggtc tgggtattaa tgttgatacc    480
ggcaatctgc agggtgatat tcgtagcagc accggctttc tgagcaccgg cagcagcagc    540
accattctga gccagaccgc agcaagcacc accagtggtg cagaaagcac cagtggcggt    600
tatcctggcg gttacccagg cggacagggt gctggaccgt taggtggcgt gcctctggtg    660
agcccgtcac tggataattt aggcggtggc ggtgcccaag ctggcctgat tcacgtgtt     720
gccaacgccc tggcgaatac gtcaacactg cgtgccgtgt acgtcgcgg tgtttcacag     780
aatacagtga ataacgtggt gcagcgcacc gtgcagtcac tggcaaacac cctgggcgtg    840
gatggcaaca atttagcccg tattgcatca caggcaatct ctcaggttcc tgccggttca    900
gatacaaatg catacgccca ggccctgtca accgccaatt tagtgacggg tggcattctg    960
aacgagcgta acattgattc actgggttca cgtgttctgt cagccgtgct gaatggcgtt   1020
tcaagtgcag cccagggttt aggcattaac gtggatacag gtaacctgca gggcgatatc   1080
cgttcaagca caggtttttct gagtacaggt agcagttcaa ccattctgtc acagacagca   1140
gcatcaacca cctcaggtgc agaaacctcc ggagggggatc c                       1181

<210> SEQ ID NO 10
<211> LENGTH: 393
<212> TYPE: PRT
<213> ORGANISM: Artificial Sequence
<220> FEATURE:
<223> OTHER INFORMATION: Synthetic sequences based on spider sequences

<400> SEQUENCE: 10

Lys Leu His Met Thr Gly Gly Tyr Pro Gly Gly Tyr Pro Gly Gly Gln
1               5                   10                  15
Gly Ala Gly Pro Leu Gly Gly Val Pro Leu Val Ser Gln Ser Leu Asp
            20                  25                  30
Asn Leu Gly Gly Gly Gly Ala Gln Ala Gly Leu Ile Ser Arg Val Ala
        35                  40                  45
Asn Ala Leu Ala Asn Thr Ser Thr Leu Arg Ala Val Leu Arg Arg Gly
    50                  55                  60
Val Ser Gln Asn Thr Val Asn Asn Val Val Gln Arg Thr Val Gln Ser
65                  70                  75                  80
Leu Ala Asn Thr Leu Gly Val Asp Gly Asn Asn Leu Ala Arg Ile Ala
                85                  90                  95
Ser Gln Ala Ile Ser Gln Val Pro Ala Gly Ser Asp Thr Asn Ala Tyr
            100                 105                 110
Ala Gln Ala Leu Ser Thr Ala Asn Leu Val Thr Gly Gly Ile Leu Asn
        115                 120                 125
Glu Arg Asn Ile Asp Ser Leu Gly Ser Arg Val Leu Ser Ala Val Leu
    130                 135                 140
Asn Gly Val Ser Ser Ala Ala Gln Gly Leu Gly Ile Asn Val Asp Thr
145                 150                 155                 160
Gly Asn Leu Gln Gly Asp Ile Arg Ser Ser Thr Gly Phe Leu Ser Thr
                165                 170                 175
Gly Ser Ser Ser Thr Ile Leu Ser Gln Thr Ala Ala Ser Thr Thr Ser
            180                 185                 190
Gly Ala Glu Ser Thr Ser Gly Gly Tyr Pro Gly Gly Tyr Pro Gly Gly
        195                 200                 205
```

Gln Gly Ala Gly Pro Leu Gly Val Pro Leu Val Ser Pro Ser Leu
            210                 215                 220

Asp Asn Leu Gly Gly Gly Ala Gln Ala Gly Leu Ile Ser Arg Val
225                 230                 235                 240

Ala Asn Ala Leu Ala Asn Thr Ser Thr Leu Arg Ala Val Leu Arg Arg
                245                 250                 255

Gly Val Ser Gln Asn Thr Val Asn Asn Val Val Gln Arg Thr Val Gln
                260                 265                 270

Ser Leu Ala Asn Thr Leu Gly Val Asp Gly Asn Asn Leu Ala Arg Ile
                275                 280                 285

Ala Ser Gln Ala Ile Ser Gln Val Pro Ala Gly Ser Asp Thr Asn Ala
        290                 295                 300

Tyr Ala Gln Ala Leu Ser Thr Ala Asn Leu Val Thr Gly Gly Ile Leu
305                 310                 315                 320

Asn Glu Arg Asn Ile Asp Ser Leu Gly Ser Arg Val Leu Ser Ala Val
                325                 330                 335

Leu Asn Gly Val Ser Ser Ala Ala Gln Gly Leu Gly Ile Asn Val Asp
                340                 345                 350

Thr Gly Asn Leu Gln Gly Asp Ile Arg Ser Ser Thr Gly Phe Leu Ser
            355                 360                 365

Thr Gly Ser Ser Ser Thr Ile Leu Ser Gln Thr Ala Ala Ser Thr Thr
    370                 375                 380

Ser Gly Ala Glu Thr Ser Gly Gly Asp
385                 390

<210> SEQ ID NO 11
<211> LENGTH: 1776
<212> TYPE: DNA
<213> ORGANISM: Artificial Sequence
<220> FEATURE:
<223> OTHER INFORMATION: Synthetic sequences based on spider sequences

<400> SEQUENCE: 11
cccgggtggc tatggtcctg gacagcaagg tcctggcggt acggtcctg gccaacaggg      60 tccctctggt ccaggcagtg cagctgccgc agccgccgca gcgggtccgg acccgggtgg    120
ctatggtcct ggacagcaag gtcctggcgg ttacggtcct ggccaacagg gtccctctgg    180
tccaggcagt gcagctgccg cagccgccgc agcgggtccg gacccgggtg gctatggtcc    240
tggacagcaa ggtcctggcg gttacggtcc tggccaacag ggtccctctg gtccaggcag    300
tgcagctgcc gcagccgccg cagcgggtcc ggacccgggt ggctatggtc tggacagca    360 aggtcctggc ggttacggtc tggccaaca gggtccctct ggtccaggca gtgcagctgc    420
cgcagccgcc gcagcgggtc cggacccggg tggctatggt cctggacagc aaggtcctgg    480
cggttacggt cctggccaac agggtccctc tggtccaggc agtgcagctg ccgcagccgc    540
cgcagcgggt ccggacccgg gtggctatgg tcctggacag caaggtcctg gcggttacgg    600
tcctggccaa cagggtccct ctggtccagg cagtgcagct gccgcagccg ccgcagcggg    660
tccggacccg gtggctatg gtcctggaca gcaaggtcct ggcggttacg gtcctggcca    720
acagggtccc tctggtccag gcagtgcagc tgccgcagcc gccgcagcgg gtccggaccc    780
gggtggctat ggtcctggac agcaaggtcc tggcggttac ggtcctggcc aacagggtcc    840
ctctggtcca ggcagtgcag ctgccgcagc gccgcagcg gtccggacc cgggtggcta    900 tggtcctgga cagcaaggtc ctggcggtta cggtcctggc aacagggtc cctctggtcc    960 aggcagtgca gctgccgcag ccgccgcagc gggtccggac ccgggtggct atggtcctgg   1020

-continued

```
acagcaaggt cctggcggtt acggtcctgg ccaacagggt ccctctggtc caggcagtgc    1080
agctgccgca gccgccgcag cgggtccgga cccgggtggc tatggtcctg acagcaagg     1140 tcctggcggt tacggtcctg gccaacaggg tccctctggt ccaggcagtg cagctgccgc    1200
agccgccgca gcgggtccgg acccgggtgg ctatggtcct ggacagcaag gtcctggcgg    1260
ttacggtcct ggccaacagg gtccctctgg tccaggcagt gcagctgccg cagccgccgc    1320
agcgggtccg acccgggtg gctatggtcc tggacagcaa ggtcctggcg gttacggtcc     1380
tggccaacag ggtccctctg gtccaggcag tgcagctgcc gcagccgccg cagcgggtcc    1440
ggacccgggt ggctatggtc ctggacagca aggtcctggc ggttacggtc ctggccaaca    1500
gggtccctct ggtccaggca gtgcagctgc cgcagccgcc gcagcgggtc cggacccggg    1560
tggctatggt cctggacagc aaggtcctgg cggttacggt cctggccaac agggtccctc    1620
tggtccaggc agtgcagctg ccgcagccgc cgcagcgggt ccggaccagg tggctatgg    1680 tcctggacag caaggtcctg gcggttacgg tcctggccaa cagggtccct ctggtccagg    1740
cagtgcagct gccgcagccg ccgcagcggg tccgga                             1776
```

<210> SEQ ID NO 12
<211> LENGTH: 591
<212> TYPE: PRT
<213> ORGANISM: Artificial Sequence
<220> FEATURE:
<223> OTHER INFORMATION: Synthetic sequences based on spider sequences

<400> SEQUENCE: 12

```
Pro Gly Gly Tyr Gly Pro Gly Gln Gln Gly Pro Gly Gly Tyr Gly Pro
1               5                   10                  15

Gly Gln Gln Gly Pro Ser Gly Pro Gly Ser Ala Ala Ala Ala Ala Ala
            20                  25                  30

Ala Ala Gly Pro Asp Pro Gly Gly Tyr Gly Pro Gly Gln Gln Gly Pro
        35                  40                  45

Gly Gly Tyr Gly Pro Gly Gln Gln Gly Pro Ser Gly Pro Gly Ser Ala
    50                  55                  60

Ala Ala Ala Ala Ala Ala Gly Pro Asp Pro Gly Gly Tyr Gly Pro
65                  70                  75                  80

Gly Gln Gln Gly Pro Gly Gly Tyr Gly Pro Gly Gln Gln Gly Pro Ser
                85                  90                  95

Gly Pro Gly Ser Ala Ala Ala Ala Ala Ala Ala Gly Pro Asp Pro
            100                 105                 110

Gly Gly Tyr Gly Pro Gly Gln Gln Gly Pro Gly Gly Tyr Gly Pro Gly
        115                 120                 125

Gln Gln Gly Pro Ser Gly Pro Gly Ser Ala Ala Ala Ala Ala Ala
    130                 135                 140

Ala Gly Pro Asp Pro Gly Gly Tyr Gly Pro Gly Gln Gln Gly Pro Gly
145                 150                 155                 160

Gly Tyr Gly Pro Gly Gln Gln Gly Pro Ser Gly Pro Gly Ser Ala Ala
                165                 170                 175

Ala Ala Ala Ala Ala Gly Pro Asp Pro Gly Gly Tyr Gly Pro Gly
            180                 185                 190

Gln Gln Gly Pro Gly Gly Tyr Gly Pro Gly Gln Gln Gly Pro Ser Gly
        195                 200                 205

Pro Gly Ser Ala Ala Ala Ala Ala Ala Ala Gly Pro Asp Pro Gly
    210                 215                 220
```

Gly Tyr Gly Pro Gly Gln Gln Gly Pro Gly Tyr Gly Pro Gly Gln
225                 230                 235                 240

Gln Gly Pro Ser Gly Pro Gly Ser Ala Ala Ala Ala Ala Ala Ala
            245                 250                 255

Gly Pro Asp Pro Gly Gly Tyr Gly Pro Gly Gln Gln Gly Pro Gly Gly
        260                 265                 270

Tyr Gly Pro Gly Gln Gln Gly Pro Ser Gly Pro Gly Ser Ala Ala Ala
        275                 280                 285

Ala Ala Ala Ala Gly Pro Asp Pro Gly Gly Tyr Gly Pro Gly Gln
    290                 295                 300

Gln Gly Pro Gly Gly Tyr Gly Pro Gly Gln Gln Gly Pro Ser Gly Pro
305                 310                 315                 320

Gly Ser Ala Ala Ala Ala Ala Ala Ala Gly Pro Asp Pro Gly Gly
        325                 330                 335

Tyr Gly Pro Gly Gln Gln Gly Pro Gly Gly Tyr Gly Pro Gly Gln Gln
        340                 345                 350

Gly Pro Ser Gly Pro Gly Ser Ala Ala Ala Ala Ala Ala Ala Gly
        355                 360                 365

Pro Asp Pro Gly Gly Tyr Gly Pro Gly Gln Gln Gly Pro Gly Gly Tyr
370                 375                 380

Gly Pro Gly Gln Gln Gly Pro Ser Gly Pro Gly Ser Ala Ala Ala Ala
385                 390                 395                 400

Ala Ala Ala Gly Pro Asp Pro Gly Gly Tyr Gly Pro Gly Gln Gln
        405                 410                 415

Gly Pro Gly Gly Tyr Gly Pro Gly Gln Gln Gly Pro Ser Gly Pro Gly
        420                 425                 430

Ser Ala Ala Ala Ala Ala Ala Ala Gly Pro Asp Pro Gly Gly Tyr
        435                 440                 445

Gly Pro Gly Gln Gln Gly Pro Gly Gly Tyr Gly Pro Gly Gln Gln Gly
        450                 455                 460

Pro Ser Gly Pro Gly Ser Ala Ala Ala Ala Ala Ala Ala Gly Pro
465                 470                 475                 480

Asp Pro Gly Gly Tyr Gly Pro Gly Gln Gln Gly Pro Gly Gly Tyr Gly
            485                 490                 495

Pro Gly Gln Gln Gly Pro Ser Gly Pro Gly Ser Ala Ala Ala Ala
            500                 505                 510

Ala Ala Ala Gly Pro Asp Pro Gly Gly Tyr Gly Pro Gly Gln Gln Gly
        515                 520                 525

Pro Gly Gly Tyr Gly Pro Gly Gln Gln Gly Pro Ser Gly Pro Gly Ser
        530                 535                 540

Ala Ala Ala Ala Ala Ala Ala Gly Pro Asp Pro Gly Gly Tyr Gly
545                 550                 555                 560

Pro Gly Gln Gln Gly Pro Gly Gly Tyr Gly Pro Gly Gln Gln Gly Pro
            565                 570                 575

Ser Gly Pro Gly Ser Ala Ala Ala Ala Ala Ala Ala Gly Pro
            580                 585                 590

<210> SEQ ID NO 13
<211> LENGTH: 62
<212> TYPE: PRT
<213> ORGANISM: Artificial Sequence
<220> FEATURE:
<223> OTHER INFORMATION: Some of the artificial sequences are based, at
      least in part, on sequences from common spiders.  Please see the
      specification for the complete explanation of the origin of the
      sequences.

<400> SEQUENCE: 13

Gly Gly Tyr Gly Pro Gly Ala Gly Gln Gln Gly Pro Gly Ser Gln Gly
1               5                   10                  15

Pro Gly Ser Gly Gly Gln Gln Gly Pro Gly Gln Gly Gly Tyr Gly
            20                  25                  30

Pro Gly Ala Gly Gln Gln Gly Pro Gly Ser Gln Gly Pro Gly Ser Gly
            35                  40                  45

Gly Gln Gln Gly Pro Gly Gly Gln Ala Ala Ala Ala Ala
        50                  55                  60

<210> SEQ ID NO 14
<211> LENGTH: 63
<212> TYPE: PRT
<213> ORGANISM: Artificial Sequence
<220> FEATURE:
<223> OTHER INFORMATION: Some of the artificial sequences are based, at
      least in part, on sequences from common spiders. Please see the
      specification for the complete explanation of the origin of the
      sequences.

<400> SEQUENCE: 14

Met Gly Gly Tyr Gly Pro Gly Ala Gly Gln Gln Gly Pro Gly Ser Gln
1               5                   10                  15

Gly Pro Gly Ser Gly Gly Gln Gln Gly Pro Gly Gly Gln Gly Gly Tyr
            20                  25                  30

Gly Pro Gly Ala Gly Gln Gln Gly Pro Gly Ser Gln Gly Pro Gly Ser
            35                  40                  45

Gly Gly Gln Gln Gly Pro Gly Gly Gln Ala Ala Ala Ala Ala Ala
        50                  55                  60

<210> SEQ ID NO 15
<211> LENGTH: 204
<212> TYPE: DNA
<213> ORGANISM: Artificial Sequence
<220> FEATURE:
<223> OTHER INFORMATION: Some of the artificial sequences are based, at
      least in part, on sequences from common spiders. Please see the
      specification for the complete explanation of the origin of the
      sequences.

<400> SEQUENCE: 15
ggcggttatg gtccgggcgc cggccagcaa ggtccgggca gccagggtcc gggcagcggt        60
ggccaacagg gtccgggtgg tcagggcggt tatggtccgg cgccggcca gcaaggtccg       120 ggcagccagg gtccgggcag cggtggccaa cagggtccgg gtggtcaggg gccgtatggt      180
ccgagcgctg cggcagcggc tgca                                              204

<210> SEQ ID NO 16
<211> LENGTH: 204
<212> TYPE: DNA
<213> ORGANISM: Artificial Sequence
<220> FEATURE:
<223> OTHER INFORMATION: Some of the artificial sequences are based, at
      least in part, on sequences from common spiders. Please see the
      specification for the complete explanation of the origin of the
      sequences.

<400> SEQUENCE: 16
ggtggttatg gtcctggtgc aggtcaacaa ggtcctggta gtcaaggtcc tggtagtggt        60
ggtcaacaag gtcctggtgg tcaaggtggt tatggtcctg gtgcaggtca acaaggtcct       120
ggtagtcaag gtcctggtag tggtggtcaa caaggtcctg gtggtcaagg tcctttatggt     180

```
cctagtgcag cagcagcagc agca                                                  204
```

<210> SEQ ID NO 17
<211> LENGTH: 204
<212> TYPE: DNA
<213> ORGANISM: Artificial Sequence
<220> FEATURE:
<223> OTHER INFORMATION: Some of the artificial sequences are based, at
      least in part, on sequences from common spiders. Please see the
      specification for the complete explanation of the origin of the
      sequences.

<400> SEQUENCE: 17

```
ggtggatatg gtcctggagc aggtcaacaa ggaccaggta gtcaaggacc tggttctgga           60
ggtcaacaag gaccaggtgg acaaggtgga tatggtcctg gagcaggtca acaaggacca          120
ggtagtcaag gacctggttc tggaggtcaa caaggaccag gtggacaagg tccttatgga          180
ccaagtgcag cagcagcagc agca                                                 204
```

<210> SEQ ID NO 18
<211> LENGTH: 207
<212> TYPE: DNA
<213> ORGANISM: Artificial Sequence
<220> FEATURE:
<223> OTHER INFORMATION: Some of the artificial sequences are based, at
      least in part, on sequences from common spiders. Please see the
      specification for the complete explanation of the origin of the
      sequences.

<400> SEQUENCE: 18

```
atgggcggtt atggtccggg cgccggccag caaggtccgg gcagccaggg tccgggcagc           60
ggtggccaac agggtccggg tggtcagggc ggttatggtc cgggcgccgg ccagcaaggt          120
ccgggcagcc agggtccggg cagcggtggc caacagggtc cgggtggtca ggggccgtat          180
ggtccgagcg ctgcggcagc ggctgca                                              207
```

<210> SEQ ID NO 19
<211> LENGTH: 207
<212> TYPE: DNA
<213> ORGANISM: Artificial Sequence
<220> FEATURE:
<223> OTHER INFORMATION: Some of the artificial sequences are based, at
      least in part, on sequences from common spiders. Please see the
      specification for the complete explanation of the origin of the
      sequences.

<400> SEQUENCE: 19

```
atgggtggtt atggtcctgg tgcaggtcaa caaggtcctg gtagtcaagg tcctggtagt           60
ggtggtcaac aaggtcctgg tggtcaaggt ggttatggtc ctggtgcagg tcaacaaggt          120
cctggtagtc aaggtcctgg tagtggtggt caacaaggtc ctggtggtca aggtccttat          180
ggtcctagtg cagcagcagc agcagca                                              207
```

<210> SEQ ID NO 20
<211> LENGTH: 207
<212> TYPE: DNA
<213> ORGANISM: Artificial Sequence
<220> FEATURE:
<223> OTHER INFORMATION: Some of the artificial sequences are based, at
      least in part, on sequences from common spiders. Please see the
      specification for the complete explanation of the origin of the
      sequences.

<400> SEQUENCE: 20

```
atgggtggat atggtcctgg agcaggtcaa caaggaccag gtagtcaagg acctggttct    60
ggaggtcaac aaggaccagg tggacaaggt ggatatggtc ctggagcagg tcaacaagga   120
ccaggtagtc aaggacctgg ttctggaggt caacaaggac caggtggaca aggtccttat   180
ggaccaagtg cagcagcagc agcagca                                       207
```

<210> SEQ ID NO 21
<211> LENGTH: 812
<212> TYPE: DNA
<213> ORGANISM: Artificial Sequence
<220> FEATURE:
<223> OTHER INFORMATION: Some of the artificial sequences are based, at
      least in part, on sequences from common spiders.  Please see the
      specification for the complete explanation of the origin of the
      sequences.

<400> SEQUENCE: 21

```
cgtattgacg taaggcgtaa aagtggtaga atgcgcctcc gcgggaatag ctcagttggt    60
agagcacgac cttgccaagg tcggggtcgc gagttcgagt ctcgtttccc gctccaaatt   120
tccaaccctc gcgtattgac gtaaggcgta aaagtggtag aatgcgcctc ctggggtatc   180
gccaagcggt aaggcaccgg ttttgatac cggcattccc tggttcgaat ccaggtaccc   240
cagccaaatt tccaaccctc gcgtattgac gtaaggcgta aaagtggtag aatgcgcctc   300
ccggcacgta gcgcagcctg gtagcgcacc gtcatgggt gtcggggtc ggaggttcaa    360 atcctctcgt gccgaccaaa tttccaaccc tcgcgtattg acgtaaggcg taaaagtggt   420
agaatgcgcc tccggggcta tagctcagct gggagagcgc ctgctttgca cgcaggaggt   480
ctgcggttcg atcccgcata gctccaccaa atttccaacc ctcgcgtatt gacgtaaggc   540
gtaaaagtgg tagaatgcgc ctccggtgag gtggccgaga ggctgaaggc gctcccctgc   600
taagggagta tgcggtcaaa agctgcatcc ggggttcgaa tccccgcctc accgccaaat   660
ttccaaccct cgcgtattga cgtaaggcgt aaaagtggta gaatgcgcct ccggtggggt   720
tcccgagcgg ccaaagggag cagactgtaa atctgccgtc acagacttcg aaggttcgaa   780
tccttccccc accaccaaat ttccaaccct cg                                 812
```

<210> SEQ ID NO 22
<211> LENGTH: 668
<212> TYPE: DNA
<213> ORGANISM: Artificial Sequence
<220> FEATURE:
<223> OTHER INFORMATION: Some of the artificial sequences are based, at
      least in part, on sequences from common spiders.  Please see the
      specification for the complete explanation of the origin of the
      sequences.

<400> SEQUENCE: 22

```
cgtattgacg taaggcgtaa aagtggtaga atgcgcctcc gcgggcatcg tataatggct    60
attacctcag ccttccaagc tgatgatgcg ggttcgattc ccgctgcccg ctccaaattt   120
ccaaccctcg cgtattgacg taaggcgtaa aagtggtaga atgcgcctcc cggcgagtag   180
cgcagcttgg tagcgcaact ggtttgggac cagtgggtcg gaggttcgaa tcctctctcg   240
ccgaccaaat ttccaaccct cgcgtattga cgtaaggcgt aaaagtggta gaatgcgcct   300
ccggtgaggt gtccgagtgg ctgaaggagc acgcctggaa agtgtgtata cggcaacgta   360 tcggggttc gaatccccc ctcaccgcca aatttccaac cctcgcgtat tgacgtaagg    420
cgtaaaagtg gtagaatgcg cctccgctga tatggctcag ttggtagagc cacccttgg   480 taagggtgag gtccccagtt cgactctggg tatcagcacc aaatttccaa ccctcgcgta   540
```

```
ttgacgtaag gcgtaaaagt ggtagaatgc gcctccgcgt tgttagctca gccggacaga    600
gcaattgcct tctgagcaat cggtcactgg ttcgaatcca gtacaacgcg ccaaatttcc    660
aaccctcg                                                              668
```

<210> SEQ ID NO 23
<211> LENGTH: 2525
<212> TYPE: DNA
<213> ORGANISM: Artificial Sequence
<220> FEATURE:
<223> OTHER INFORMATION: This is a sequence from a vector.

<400> SEQUENCE: 23

```
agcttctttc gggctttgtt agcagccgga tcctcgagca tatgcttgtc gtcgtcgtcg     60
atatggccgc tgctgtgatg atgatgatga tgatgatgat gatggcccat ggtatatctc    120
cttcttaaag ttaaacaaaa ttatttctag aggggaattg ttatccgctc acaattcccc    180
tatagtgagt cgtattaatt tcgcgggatc gagatctgac ctgttatcgc acaatgattc    240
ggttatactg ttcgccgttg ccaacagga ccgcctataa aggccaaaaa ttttattgtt    300
agctgagtca ggagatgcgg atgttaaagc gtgaaatgaa cattgccgat tatgatgccg    360
aactgtggca ggctatggag caggaaaaag tacgtcagga agagcacatc gaactgatcg    420
cctccgaaaa ctacaccagc ccgcgcgtaa tgcaggcgca gggttctcag ctgaccaaca    480
aatatgctga aggttatccg ggcaaacgct actacggcgg ttgcgagtat gttgatatcg    540
ttgaacaact ggcgatcgat cgtgcgaaag aactgttcgg cgctgactac gctaacgtcc    600
agccgcactc cggctcccag gctaactttg cggtctacac cgcgctgctg aaccaggtg    660 ataccgttct gggtatgaac ctggcgcatg gcggtcacct gactcacggt ctccgtta    720 acttctccgg taaactgtac aacatcgttc cttacggtat tgatgctacc ggtcatatcg    780
actacgccga tctggaaaaa caagccaaag aacacaagcc gaaaatgatt atcggtggtt    840
tctctgcata ttccggcgtg gtggactggg cgaaaatgcg tgaaatcgct gacagcatcg    900
gtgcttacct gttcgttgat atggcgcacg ttgcgggcct ggttgctgct ggcgtctacc    960
cgaacccggt tcctcatgct cacgttgtta ctaccaccac tcacaaaacc ctggcgggtc   1020
cgcgcggcgg cctgatcctg gcgaaaggtg gtagcgaaga gctgtacaaa aaactgaact   1080
ctgccgtttt ccctggtggt cagggcggtc cgttgatgca cgtaatcgcc ggtaaagcgg   1140
ttgctctgaa agaagcgatg gagcctgagt tcaaaactta ccagcagcag gtcgcgaaaa   1200
acgctaaagc gatggtagaa gtgttcctcg agcgcggcta caagtggttt ccggcggca   1260 ctgataacca cctgttcctg gttgatctgg ttgataaaaa cctgaccggt aaagaagcag   1320
acgccgctct gggccgtgct aacatcaccg tcaacaaaaa cagcgtaccg aacgatccga   1380
agagcccgtt tgtgacctcc ggtattcgcg tgggtactcc ggcaattacg cgtcgcggct   1440
tcaaagaagc agaagcgaaa gaactggctg gctggatgtg tgacgtgctg gacagcatca   1500
atgatgaagc cgttatcgag cgcatcaaag gtaaagttct cgacatctgc gcacgttacc   1560
cggtttacgc ataagcgaaa cggtgatttg ctgacaatgt gctcgttgtt catgttggat   1620
gcggcatgaa cacgtcgacc gtagcccgag acgataagtt cgcttaccgg ctcgaatgaa   1680
gagagcttct ctcgatattc agtgcagaat gaaaatcagg tagccgagtt ccaggatgcg   1740
ggcatcgtat aatggctatt acctcagcct tccaagctga tgatgcgggt tcgattcccg   1800
ctgcccgctc aagatgtgc tgatatagct cagttggtag agcgcaccct tggtaagggt   1860
```

```
gaggtcggca gttcgaatct gcctatcagc accacttctt ttctcctccc tgttttttcc   1920
ttctgtttat tgcattcaac aagtcgggca tgttgcaagc ttcttgcaat cggtgtggaa   1980
aacggtagta ttagcagcca cgagtcggca cgtagcgcag cctggtagcg caccgtcatg   2040
gggtgtcggg ggtcggaggt tcaaatcctc tcgtgccgac caaaaatccc aagaaaaaac   2100 caaccttac ggttggtttt tttatatctg caattaattc gataaacaga ccgtgacaca    2160
tcacgaattc ctcgcaccac gactttaaag aattgaacta aaaattcaaa aagcagtatt   2220
tcggcgagta gcgcagcttg gtagcgcaac tggtttggga ccagtgggtc ggaggttcga   2280
atcctctctc gccgaccaat tttgaacccc gcttcggcgg ggttttttgt tttctgtgca   2340
tttcgtcact ttcccgcatg caccattcct tgcggcggcg gtgctcaacg gcctcaacct   2400
actactgggc tgcttcctaa tgcaggagtc gcataaggga gagcgtcgag atcccggaca   2460
ccatcgaatg gcgcaaaacc tttcgcggta tggcatgata gcgcccggaa gagagtcaat   2520
tcagg                                                                2525

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
tgccacctga cgtctaagaa                                                 20

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
attaccgcct ttgagtgagc                                                 20

<210> SEQ ID NO 26
<211> LENGTH: 29
<212> TYPE: PRT
<213> ORGANISM: Artificial Sequence
<220> FEATURE:
<223> OTHER INFORMATION: Some of the artificial sequences are based, at
      least in part, on sequences from common spiders.  Please see the
      specification for the complete explanation of the origin of the
      sequences.

<400> SEQUENCE: 26

Gly Gly Tyr Gly Pro Gly Ala Gly Gln Gln Gly Pro Gly Ser Gln Gly
1               5                   10                  15

Pro Gly Ser Gly Gly Gln Gln Gly Pro Gly Gly Gln Arg
            20                  25

<210> SEQ ID NO 27
<211> LENGTH: 354
<212> TYPE: PRT
<213> ORGANISM: Artificial Sequence
<220> FEATURE:
<223> OTHER INFORMATION: Some of the artificial sequences are based, at
      least in part, on sequences from common spiders.  Please see the
      specification for the complete explanation of the origin of the
      sequences.

<400> SEQUENCE: 27
```

-continued

```
Lys Leu His Met Gly Ser Thr Gly Pro Gly Pro Gly Gly Ala Gly
 1               5              10              15

Pro Gly Gly Ala Gly Pro Gly Gly Ala Gly Pro Gly Gly Ala Gly Pro
                20              25              30

Gly Gly Ala Gly Pro Gly Gly Ala Gly Pro Gly Gly Ala Gly Pro Gly
             35              40              45

Gly Ala Gly Ser Gly Pro Gly Ser Ala Ala Ala Ala Ala Ala Ala
         50              55              60

Gly Pro Gly Gly Ala Gly Pro Gly Gly Ala Gly Pro Gly Gly Ala Gly
 65              70              75              80

Pro Gly Gly Ala Gly Pro Gly Gly Ala Gly Pro Gly Gly Ala Gly Pro
                85              90              95

Gly Gly Ala Gly Pro Gly Gly Ala Gly Pro Gly Gly Ala Gly Pro Gly
            100             105             110

Gly Ala Gly Pro Ser Gly Pro Gly Ser Ala Ala Ala Ala Ala Ala Ala
        115             120             125

Ala Gly Pro Gly Gly Ala Gly Pro Gly Gly Ala Gly Pro Gly Gly Ala
    130             135             140

Gly Pro Gly Gly Ala Gly Pro Gly Gly Ala Gly Pro Gly Gly Ala Gly
145             150             155             160

Pro Ser Gly Pro Gly Ser Ala Ala Ala Ala Ala Ala Ala Gly Pro
                165             170             175

Gly Gly Ala Gly Pro Gly Gly Ala Gly Pro Gly Gly Ala Gly Pro Gly
            180             185             190

Gly Ala Gly Pro Gly Gly Ala Gly Pro Gly Gly Ala Gly Pro Gly Gly
        195             200             205

Ala Gly Pro Gly Gly Ala Gly Pro Gly Gly Ala Gly Pro Gly Gly Ala
    210             215             220

Gly Pro Gly Gly Ala Gly Pro Gly Gly Ala Gly Pro Ser Gly Pro Gly
225             230             235             240

Ser Ala Ala Ala Ala Ala Ala Ala Gly Pro Gly Gly Ala Gly Pro
                245             250             255

Gly Gly Ala Gly Pro Gly Gly Ala Gly Pro Gly Gly Ala Gly Pro Gly
            260             265             270

Gly Ala Gly Pro Gly Gly Ala Gly Pro Gly Gly Ala Gly Pro Gly Gly
        275             280             285

Ala Gly Pro Gly Gly Ala Gly Pro Gly Gly Ala Gly Pro Gly Gly Ala
    290             295             300

Gly Pro Gly Gly Ala Gly Pro Gly Gly Ala Gly Pro Gly Gly Ala Gly
305             310             315             320

Pro Gly Gly Ala Gly Pro Gly Gly Ala Gly Pro Ser Gly Pro Gly Ser
                325             330             335

Ala Ala Ala Ala Ala Ala Ala Ser Gly Gly Pro Asp Ile Leu Glu
                340             345             350

Gly Ser
```

What is claimed is:

1. An expression system, comprising:
   a host cell,
   a synthetic spider silk polypeptide-encoding nucleotide sequence which encodes at least one polypeptide sequence selected from the group consisting of SEQ ID NO:2, SEQ ID NO:4, SEQ ID NO:6, SEQ ID NO:8, SEQ ID NO:10, SEQ ID NO:12, SEQ ID NO:13, SEQ ID NO:14, and SEQ ID NO: 27; and
   a nucleotide sequence selected from the group consisting of:
   at least one synthetic tRNA molecule-encoding nucleotide sequence, and
   a synthetic serine hydroxymethyl transferase (SHMT)-encoding nucleotide sequence.

2. The expression system of claim 1, wherein the expression system comprises the at least one synthetic tRNA molecule-encoding nucleotide sequence.

3. The expression system of claim 2, wherein the at least one synthetic tRNA molecule-encoding nucleotide sequence when expressed is a tRNA that binds to an amino acid selected from the group consisting of glycine, glutamine, proline, alanine, serine, and tyrosine.

4. The expression system of claim 1, wherein the expression system comprises the synthetic SHMT-encoding nucleotide sequence.

5. The expression system of claim 1, wherein the expression system comprises
the at least one synthetic tRNA molecule-encoding nucleotide sequence, and
the synthetic SHMT-encoding nucleotide sequence.

6. The expression system of claim 1, wherein the synthetic nucleotide sequences are provided on at least one vector.

7. The expression system of claim 1, wherein the host cell is an *E. coli* cell.

8. The expression system of claim 1, wherein the synthetic spider silk polypeptide-encoding nucleotide sequence encodes for spider silk proteins selected from the group consisting of MaSP1, MaSP2, MiSP, MiSp2, AcSP, FLYS, and FLAS.

9. The expression system of claim 1, where the nucleotide sequences encoding the at least one polypeptide sequence are sequentially arranged and provide for a single recombinant spider silk polypeptide.

10. The expression system of claim 1, wherein a GC % of the synthetic spider silk polypeptide-encoding nucleotide sequence is within 15 percentage points of a GC % of the host cell.

11. The expression system of claim 1, wherein the at least one synthetic tRNA molecule-encoding nucleotide sequence encodes a tRNA having an anticodon that corresponds to a codon provided in a synthetic spider silk polypeptide-encoding nucleotide sequence.

12. A method of upregulating synthetic spider silk polypeptide production in a host cell, the method comprising:
providing in the host cell a synthetic spider silk polypeptide-encoding nucleotide sequence which encodes at least one polypeptide sequence selected from the group consisting of SEQ ID NO:2, SEQ ID NO:4, SEQ ID NO:6, SEQ ID NO:8, SEQ ID NO:10, SEQ ID NO:12, SEQ ID NO:13, SEQ ID NO:14, and SEQ ID NO: 27; and
providing in the host cell:
at least one synthetic tRNA molecule-encoding nucleotide sequence, or
a synthetic SHMT-encoding nucleotide sequence.

13. The method of claim 12, wherein the at least one synthetic tRNA molecule-encoding nucleotide sequence is provided.

14. The method of claim 12, wherein the synthetic SHMT-encoding nucleotide sequence is provided.

15. The method of claim 12, wherein the at least one synthetic tRNA molecule-encoding nucleotide sequence and the synthetic SHMT-encoding nucleotide sequence are provided.

16. The method of claim 12, wherein the GC % of the synthetic spider silk polypeptide-encoding nucleotide sequence is within 15 percentage points of the GC % of the host cell.

17. The method of claim 12, wherein the at least one synthetic tRNA molecule-encoding nucleotide sequence provides for a tRNA molecule having a anticodon that corresponds to a codon provided in a synthetic spider silk polypeptide-encoding nucleotide sequence.

18. An expression system, comprising:
a host cell,
a synthetic spider silk polypeptide-encoding nucleotide sequence which encodes at least one polypeptide sequence selected from the group consisting of SEQ ID NO:2, SEQ ID NO:4, SEQ ID NO:6, SEQ ID NO:8, SEQ ID NO:10, SEQ ID NO:12, SEQ ID NO:13, and SEQ ID NO:14; and
a nucleotide sequence selected from the group consisting of:
at least one synthetic tRNA molecule-encoding nucleotide sequence, and
a synthetic serine hydroxymethyl transferase (SHMT)-encoding nucleotide sequence.

* * * * *